US008691961B1

(12) United States Patent
Puffer et al.

(10) Patent No.: US 8,691,961 B1
(45) Date of Patent: Apr. 8, 2014

(54) FLAVIVIRUS REPORTER VIRUS AND METHODS OF MAKING AND USING THE SAME

(75) Inventors: Bridget Puffer, Corning, NY (US); Kimberly-Anne Mattia, Philadelphia, PA (US)

(73) Assignee: Integral Molecular, Inc., Philadelphia, PA (US)

( * ) Notice: Subject to any disclaimer, the term of this patent is extended or adjusted under 35 U.S.C. 154(b) by 376 days.

(21) Appl. No.: 12/942,632

(22) Filed: Nov. 9, 2010

Related U.S. Application Data

(60) Provisional application No. 61/259,279, filed on Nov. 9, 2009.

(51) Int. Cl.
*C07H 21/00* (2006.01)
*A61K 39/12* (2006.01)

(52) U.S. Cl.
USPC .................. 536/23.72; 435/320.1; 424/218.1

(58) Field of Classification Search
None
See application file for complete search history.

(56) References Cited

U.S. PATENT DOCUMENTS

| | | | | |
|---|---|---|---|---|
| 6,893,866 | B1 | 5/2005 | Westaway et al. | |
| 2004/0265338 | A1 | 12/2004 | Pang et al. | |
| 2008/0318208 | A1* | 12/2008 | Puffer et al. | 435/5 |
| 2009/0324623 | A1* | 12/2009 | Frolov et al. | 424/184.1 |

FOREIGN PATENT DOCUMENTS

WO WO 2008/051266 A2 * 5/2008

OTHER PUBLICATIONS

Khromykh, A. A., et al., Encapsidation of the flavivirus kunjin replicon RNA by using a complementation system providing Kunjin virus structural proteins in trans, J Virol. Jul. 1998;72(7):5967-77.
Khromykh, A. A., et al., Subgenomic replicons of the flavivirus Kunjin: construction and applications, J Virol. Feb. 1997;71(2):1497-505.
Harvey, T. J., et al., Tetracycline-inducible packaging cell line for production of flavivirus replicon particles, J Virol. Jan. 2004;78(1):531-8.
Holden, K. L., et al., Inhibition of dengue virus translation and RNA synthesis by a morpholino oligomer targeted to the top of the terminal 3' stem-loop structure, Virology. Jan. 20, 2006;344(2):439-52.
Pierson, T. C., et al., An infectious West Nile virus that expresses a GFP reporter gene, Virology. Mar. 30, 2005;334(1):28-40.
Gibbons, R. V., et al., Dengue: an escalating problem, BMJ. Jun. 29, 2002;324(7353):1563-6.
Lindenbach, B.D. and Rice, C. M.; Chapter 32 Flaviviridae: The Viruses and Their Replication, Fields Virology, 1996;2:931-959.
Kuhn, R. J., et al., Structure of dengue virus: implications for flavivirus organization, maturation, and fusion, Cell. Mar. 8, 2002;108(5):717-25.
Mukhopadhyay, S., et al, Structure of West Nile virus, Science. Oct. 10, 2003;302(5643):248.
Zhang, Y., et al., Structures of immature flavivirus particles, EMBO J. Jun. 2, 2003;22(11):2604-13.
Navarro-Sanchez, E., et al., Dendritic-cell-specific ICAM3-grabbing non-integrin is essential for the productive infection of human dendritic cells by mosquito-cell-derived dengue viruses, EMBO Rep. Jul. 2003;4(7):723-8.
Tassaneetrithep, B., et al., DC-SIGN (CD209) mediates dengue virus infection of human dendritic cells, J Exp Med. Apr. 7, 2003;197(7):823-9.
Khromykh, A. A., et al., Efficient trans-complementation of the flavivirus kunjin NS5 protein but not of the NS1 protein requires its coexpression with other components of the viral replicase, J Virol. Dec. 1999;73(12):10272-80.
Khromykh, A. A., et al., cis- and trans-acting elements in flavivirus RNA replication, J Virol. Apr. 2000;74(7):3253-63.
Burke, D. S. and Monath, T. P., Chapter 33 Flaviviruses, Fields Virology, 1996;2:961-1034.
Khromykh, A. A., et al., Significance in replication of the terminal nucleotides of the flavivirus genome, J Virol. Oct. 2003;77(19):10623-9.
Novak, J. E., et al., Coupling between genome translation and replication in an RNA virus, Genes Dev. Jul. 15, 1994;8(14):1726-37.
Mackenzie, J. M., et al., Markers for trans-Golgi Membranes and the Intermediate Compartment Localize to Induced Membranes with Distinct Replication Functions in Flavivirus-Infected Cells, J Virol, Nov. 1999;73:9555-67.
Mackenzie, J. M., et al., Subcellular localization and some biochemical properties of the flavivirus Kunjin nonstructural proteins NS2A and NS4A, Virology. Jun. 5, 1998;245(2):203-15.
Lorenz, I. C., et al., Intracellular assembly and secretion of recombinant subviral particles from tick-borne encephalitis virus, J Virol. Apr. 2003;77(7):4370-82.
Mackenzie, J. M., et al., Assembly and maturation of the flavivirus Kunjin virus appear to occur in the rough endoplasmic reticulum and along the secretory pathway, respectively, J Virol. Nov. 2001;75(22):10787-99.
Heinz, F. X., et al., Structures and mechanisms in flavivirus fusion, Adv Virus Res. 2000;55:231-69.
Lorenz, I. C., et al., Folding and dimerization of tick-borne encephalitis virus envelope proteins prM and E in the endoplasmic reticulum, J Virol. Jun. 2002;76(11):5480-91.
Russel, P. K., et al., Dengue virus identification by the plaque reduction neutralization test, J Immunol. Aug. 1967;99(2):291-6.
Elshuber, S., et al., Cleavage of protein prM is necessary for infection of BHK-21 cells by tick-borne encephalitis virus, J Gen Virol. Jan. 2003;84(Pt 1):183-91.
Ferlenghi, I., et al., Molecular organization of a recombinant subviral particle from tick-borne encephalitis virus, Mol Cell. Mar. 2001;7(3):593-602.
Heinz, F.X., et al., Recombinant and virion-derived soluble and particulate immunogens for vaccination against tick-borne encephalitis, Vaccine. Dec. 1995;13(17):1636-42.

(Continued)

*Primary Examiner* — Stacy B. Chen
(74) *Attorney, Agent, or Firm* — Pepper Hamilton LLP

(57) ABSTRACT

The present invention relates to the production and uses of flavivirus replicons and flavivirus particles and reporter virus particles. The present invention relates to the production and uses of chimeric and codon-optimized flavivirus virus replicons and flavivirus virus particles and reporter virus particles.

16 Claims, 9 Drawing Sheets

(56) References Cited

OTHER PUBLICATIONS

Kliks, S. C., et al., Antibody-dependent enhancement of dengue virus growth in human monocytes as a risk factor for dengue hemorrhagic fever, Am J Trop Med Hyg. Apr. 1989;40(4):444-51.

Pugachev, K. V., et al., Traditional and novel approaches to flavivirus vaccines, Int J Parasitol. May 2003;33(5-6):567-82.

Halstead, S. B., Pathogenesis of dengue: challenges to molecular biology, Science. Jan. 29, 1988;239(4839):476-81.

Halstead, S. B., Antibody, macrophages, dengue virus infection, shock, and hemorrhage: a pathogenetic cascade, Rev Infect Dis. May-Jun. 1989;11 Suppl 4:S830-9.

Halstead, S. B., et al., Observations related to pathogenesis of dengue hemorrhagic fever. IV. Relation of disease severity to antibody response and virus recovered, Yale J Biol Med. Apr. 1970;42(5):311-28.

Halstead, S. B., et al., Dengue viruses and mononuclear phagocytes. I. Infection enhancement by non-neutralizing antibody, J Exp Med. Jul. 1, 1977;146(1):201-17.

Bray, M., et al., Construction of intertypic chimeric dengue viruses by substitution of structural protein genes, Proc Natl Acad Sci U S A. Nov. 15, 1991;88(22):10342-6.

Chambers, T. J., et al., Yellow Fever/Japanese Encephalitis chimeric Viruses: Construction and Biological Properties, Journal of Virology, Apr. 1999:3095-3101.

Clyde, K., et al., The capsid-coding region hairpin element (cHP) is a critical determinant of dengue virus and West Nile virus RNA synthesis, Virology. Sep. 30, 2008;379(2):314-23.

Pletnev, A. G., et al., West Nile virus/dengue type 4 virus chimeras that are reduced in neurovirulence and peripheral virulence without loss of immunogenicity or protective efficacy, Proc Natl Acad Sci U S A. Mar. 5, 2002;99(5):3036-41.

\* cited by examiner

FIG. 1

| | | | | |
|---|---|---|---|---|
| DENV2wt | Capsid | PreMembrane | Envelope | |
| DENV3opt | | | | |
| DENV2/3opt | | | | |
| DENV4wt | | | | |
| DENV2/4wt | | | | |
| DENV2/4opt | | | | |

Cleavage site position: P4 P3 P2 P1 P1'

| | P4 | P3 | P2 | P1 | P1' | |
|---|---|---|---|---|---|---|
| DENV2 S16803 | R | R | R | R | S | SEQ ID NO: 24 |
| DENV1 WestPac | R | R | K | R | S | SEQ ID NO: 25 |
| DENV3 CH53489 | K | R | K | K | T | SEQ ID NO: 26 |
| DENV4 TVP-360 | G | R | K | R | S | SEQ ID NO: 27 |
| DENV2/1 Chimera | R | R | R | R | S | SEQ ID NO: 24 |
| DENV2/3 Chimera | R | R | R | R | S | SEQ ID NO: 24 |
| DENV2/4 Chimera | R | R | R | R | S | SEQ ID NO: 24 |
| | R | R | R | R | S | SEQ ID NO: 24 |

FIG. 3

% Infection-Harvest A

DENV4 - Original Plasmid
37C - 100ng Dox
40X Magnification

DENV2 CA/DENV WT pRME
37C - 100ng Dox
40X Magnification

DENV2 CA/DENV4 CO pRME
37C - 100ng Dox
40X Magnification

A.

B.

A.

B.

SEQUENCE LISTING

<160> NUMBER OF SEQ ID NOS: 27

<210> SEQ ID NO 1
<211> LENGTH: 2325
<212> TYPE: DNA
<213> ORGANISM: artificial sequence
<220> FEATURE:
<223> OTHER INFORMATION: Chimeric nucleotide sequence

<400> SEQUENCE: 1

```
atgaataacc aacggaaaaa ggcgaaaaac acgcctttca atatgctgaa acgcgagaga      60
aaccgcgtgt cgactgtgca acagctgaca aagagattct cacttggaat gctgcaggga     120
cgaggaccat taaaactgtt catggccctg gtggcgttcc ttcgtttcct aacaatccca     180
ccaacagcag ggatattgaa gagatgggga acaattaaaa aatcaaaagc cattaatgtt     240
ttgagagggt tcaggaaaga gattggaagg atgctgaaca tcttgaatag agacgcaga     300 tccagcttat gtctgatgat gatgctgcct gccaccctcg ctttccacct gacgagtcga     360
gatggagaac cccggatgat cgtgggcaag aatgaacggg gcaaaagtct gcttttcaaa     420
acagccagtg gcattaacat gtgtacactg atcgccatgg acctgggcga gatgtgtgac     480
gatactgtca catacaaatg tccacacata gccgaggtgg agcccgagga catcgactgc     540
tggtgcaacc ttaccagtac ctgggtgacg tatggaacat gtaaccaggc cggcgagcac     600
aggcgggata agagatccgt tgctctcgca ccacatgtgg gcatgggcgct ggataccagg     660 acacaaacct ggatgtcagc cgaggagcc tggagacagg ttgagaaagt tgagacctgg     720
gctctgaggc acccgggctt caccatactt gccctgtttc tggctcacta catcggaacc     780
tccctgaccc agaaggttgt gatctttatc ttgctgatcc tggtgaccc ttcaatggct     840 atgaggtgcg tgggtgtggg caatcgggac tttgtcgagg ggctctcagg ggccacatgg     900
gtggatgtgg tgctggaaca cggggggctgc gtcaccacga tggccaagaa taagccgaca     960
ctggatattg aacttcagaa gacagaggcc acgcaactgg caactctgcg caaactgtgt    1020
atcgagggca agataactaa tattacaact gacagccggt gtcccactca gggtgaagcc    1080
atcctcccag aagagcagga ccaaaactac gtgtgtaaac atacatacgt tgatcgtggg    1140
tggggaaacg gatgcggtct gttcgggaag ggatctctgg tgacctgtgc caagttccag    1200
tgtctggagt caatcgaggg aaaagtggtg cagcacgaaa atctcaaata cactgtgata    1260
atcacagttc acacgggcga ccaacaccag gttggcaatg agactcaggg ggtgaccgct    1320
gagatcaccc ctcaagcctc aacagtggag gctattcttc ccgaatatgg caccctgggg    1380
ctggagtgct ccccacgcac gggtctggac tttaatgaga tgatactgct gactatgaag    1440
aataaggctt ggatggtgca cagacagtgg tttttcgatt tgccactgcc ttggaccagc    1500
ggggcaacta ctgaaacccc cacctggaac aggaaggaac tgctggtgac tttttaagaac    1560 gctcatgcta aaaagcagga ggtggtggtc ttgggcagtc aggagggagc catgcacacg    1620
gccttgactg gcgccaccga gatccagaat tcaggggca ccagtatctt tgcaggacac    1680
```

-continued

| | |
|---|---|
| ctcaagtgca ggctgaaaat ggataagttg gagctgaagg gaatgagcta tgccatgtgc | 1740 |
| ctgaatacgt tcgtgcttaa gaaagaggtt agcgagacgc agcacgggac catcctcatt | 1800 |
| aaggtggaat ataagggaga ggacgcccca tgcaaaattc cctttagtac tgaagatggc | 1860 |
| cagggcaaag ctcataacgg aaggctcatc accgctaacc ccgtggtgac caaaaaagag | 1920 |
| gagccggtta acattgaggc tgaaccacct ttcggcgaat ctaatatcgt gatagggatc | 1980 |
| ggcgacaagg cacttaagat caactggtat aaaaagggct catccatcgg caagatgttc | 2040 |
| gaagctacag ctagaggggc tagaagaatg gccattctcg gagatacagc ctgggacttt | 2100 |
| ggtagtgtgg gcggggtgct caatagtctg ggcaagatgg tccaccagat cttcggttct | 2160 |
| gcctacactg ctctgttcag tggggtcagc tggattatga agatcggcat tggtgtgctt | 2220 |
| ctcacttgga tcggactgaa tagcaagaac acttctatga gcttttcatg catagccatc | 2280 |
| ggcatcatta ctctgtacct cggcgccgtg gtgcaggccg cttag | 2325 |

<210> SEQ ID NO 2
<211> LENGTH: 2328
<212> TYPE: DNA
<213> ORGANISM: artificial sequence
<220> FEATURE:
<223> OTHER INFORMATION: chimeric sequence

<400> SEQUENCE: 2

| | |
|---|---|
| atgaataacc aacggaaaaa ggcgaaaaac acgcctttca atatgctgaa acgcgagaga | 60 |
| aaccgcgtgt cgactgtgca acagctgaca aagagattct cacttggaat gctgcaggga | 120 |
| cgaggaccat taaaactgtt catggccctg gtggcgttcc ttcgtttcct aacaatccca | 180 |
| ccaacagcag ggatattgaa gagatgggga caattaaaaa atcaaaagc cattaatgtt | 240 |
| ttgagagggt tcaggaaaga gattggaagg atgctgaaca tcttgaatag agacgcaga | 300 |
| tccacgataa cattgctgtg cttgattccc accgtaatgg cgtttcactt gtcaacaaga | 360 |
| gatggcgaac ccctcatgat agtggcaaaa catgaaaggg ggagacctct cttgtttaag | 420 |
| acaacagagg ggatcaacaa atgcactctc attgccatgg acttgggtga atgtgtgag | 480 |
| gacactgtca cgtataaatg ccccctactg gtcaataccg aacctgaaga cattgattgc | 540 |
| tggtgcaacc tcacgtctac ctgggtcatg tatgggacat gcaccagag cggagaacgg | 600 |
| agacgagaga agcgctcagt agctttaaca ccacattcag gaatgggatt ggaaacaaga | 660 |
| gctgagacat ggatgtcatc ggaagggct tggaagcatg ctcagagagt agagagctgg | 720 |
| atactcagaa acccaggatt cgcgctcttg gcaggattta tggcttatat gattgggcaa | 780 |
| acaggaatcc agcgaactgt cttctttgtc ctaatgatgc tggtcgcccc atcctacgga | 840 |
| atgcgatgcg taggagtagg aaacagagac tttgtggaag agtctcagg tggagcatgg | 900 |
| gtcgacctgg tgctagaaca tggaggatgc gtcacaacca tggcccaggg aaaaccaacc | 960 |
| ttggattttg aactgactaa gacaacagcc aaggaagtgg ctctgttaag aacctattgc | 1020 |
| attgaagcct caatatcaaa cataactacg gcaacaagat gtccaacgca aggagagcct | 1080 |
| tatctgaaag aggaacagga ccaacagtac atttgccgga gagatgtggt agacagaggg | 1140 |
| tgggcaatg gctgtggcct gtttggaaaa ggaggagttg tgacatgtgc gaagttttca | 1200 |
| tgttcgggga agataacagg caattggtc caaattgaga acctcgaata cacagtggtt | 1260 |
| gtaacagtcc acaatggaga cacccatgca gtaggaaatg acacatccaa tcatggagtt | 1320 |
| acagccatga taactcccag gtcaccatcg gtggaagtca attgccgga ctatggagaa | 1380 |
| ctaacactcg attgtgaacc caggtctgga attgacttta atgagatgat tctgatgaaa | 1440 |

```
atgaaaaaga aaacatggct cgtgcataag caatggtttt tggatctgcc tcttccatgg    1500
acagcaggag cagacacatc agaggttcac tggaattaca aagagagaat ggtgacattt    1560
aaggttcctc atgccaagag acaggatgtg acagtgctgg atctcaggaa ggagccatg     1620 cattctgccc tcgctggagc cacagaagtg gactccggtg atggaaatca catgtttgca    1680
ggacatctca agtgcaaagt ccgcatggag aaattgagaa tcaagggaat gtcatacacg    1740
atgtgttcag gaaagttttc aattgacaaa gagatggcag aaacacagca tgggacaaca    1800
gtggtgaaag tcaagtatga aggtgctgga gctccgtgta agtccccat agagataaga     1860 gatgtaaaca aggaaaaagt ggttgggcgt atcatctcat ccacccctt ggctgagaat     1920 accaacagtg taaccaacat agaattagaa ccccccttg gggacagcta catagtgata     1980
ggtgttggaa gcagcgcatt aacactccat tggttcagga agggagttc cattggcaag     2040 atgtttgagt ccacatacag aggtgcaaaa cgaatggcca ttctaggtga aacagcttgg    2100
gattttggtt ccgttggtgg actgttcaca tcattgggaa aggctgtgca ccaggttttt    2160
ggaagtgtgt atacaaccat gtttggagga gtctcatgga tgattagaat cctaattggg    2220
ttcttagtgt tgtggattgg cacgaactca aggaacactt caatggccat gacgtgcata    2280
gctgttggag gaatcactct gtttctgggc ttcacagttc aggcatga                2328

<210> SEQ ID NO 3
<211> LENGTH: 2328
<212> TYPE: DNA
<213> ORGANISM: artificial sequence
<220> FEATURE:
<223> OTHER INFORMATION: chimeric sequence

<400> SEQUENCE: 3
atgaataacc aacggaaaaa ggcgaaaaac acgcctttca atatgctgaa acgcgagaga      60
aaccgcgtgt cgactgtgca acagctgaca aagagattct cacttggaat gctgcaggga     120
cgaggaccat taaaactgtt catggccctg gtggcgttcc ttcgtttcct aacaatccca     180
ccaacagcag gatattgaa gagatgggga acaattaaaa aatcaaaagc cattaatgtt      240
ttgagagggt tcaggaaaga gattggaagg atgctgaaca tcttgaatag gagacgcaga     300
tccaccatca cactgctgtg cctgattccc actgtgatgg ccttccacct gtccacccgg     360
gacggcgagc tctgatgat cgtggctaag catgaaagag ggaggccact gctgtttaaa      420
acaactgagg gaattaacaa gtgtaccctg atcgctatgg acctgggcga atgtgcgag      480 gacacagtga cttacaaatg tccccctgctg gtgaataccg aacctgagga tattgactgc    540
tggtgtaacc tgacatctac ttgggtcatg tatgggacct gcacacagag tggagaacgc    600
cggagagaga agaggtcagt ggctctgact ccacacagcg gcatgggct ggaaacccgc      660 gccgagacat ggatgtcctc tgaaggagct tggaaacatg cccagcgggt ggagagttgg    720
atcttgagaa atcccggctt cgctctgctg gccgggttta tggcttacat gattggacag    780
actggcatcc agaggaccgt gttctttgtg ctgatgatgc tggtggcccc tagctacggc    840
atgcgctgcg tgggagtggg caaccgggat ttcgtggaag gggtgagcgg aggcgcttgg    900
gtggacctgg tgctggagca ggggggatgc gtgacaacta tgcccagggg caagccaacc    960 ctggatttg aactgacaaa aactaccgct aaggaggtgg ccctgctgag aacatactgt    1020
attgaggcca gcatctctaa tattactacc gccacaaggt gccccactca gggggagcct    1080
tatctgaaaa agagcagga ccagcagtac atctgtcgcc gggatgtggt ggacagagga    1140
tggggcaacg gtgcggact gttcggcaag gggggagtgg tgacctgtgc taagttcagc    1200
```

```
tgctcaggca agattacagg gaatctggtg cagatcgaaa acctggagta tactgtggtg    1260
gtgaccgtgc ataatggaga tacacacgcc gtgggcaacg acactagcaa tcatggggtg    1320
accgctatga ttacaccaag gtcccctct gtggaagtga aactgcctga ttacggagag    1380
ctgactctgg actgtgaacc acgcagtggc atcgatttca cgagatgat tctgatgaag    1440 atgaaaaaga aaacctggct ggtgcacaag cagtggtttc tggacctgcc cctgccttgg    1500
acagccgggg ctgatacttc agaagtgcat tggaattata aagagcggat ggtgaccttc    1560
aaggtgccac acgccaaaag acaggacgtg acagtgctgg aagccagga aggcgctatg    1620 cattccgccc tggctggggc cactgagtg gattctggag acggcaacca catgtttgct    1680
gggcatctga agtgcaaagt gaggatggaa aagctgcgca tcaaaggaat gagttacacc    1740
atgtgctccg gcaagttcag cattgataaa gagatggccg aaacacagca cgggactacc    1800
gtggtgaagg tgaaatatga gggagctggc gccccctgca aggtgcctat cgaaattcgg    1860
gacgtgaaca aggagaaggt ggtggggaga atcatttcct ctacaccact ggctgagaac    1920
actaatagtg tgaccaacat cgagctggag ccccctttg gagattcata cattgtgatc    1980
ggcgtgggga gctccgccct gacactgcac tggttcagga agggatctag tattggcaag    2040
atgtttgagt ctacttatag gggagcaaag aggatggcaa tcctgggaga ccgcatgg    2100 gacttcggca gcgtgggagg actgtttaca agcctgggca aggccgtgca ccaggtgttc    2160
gggtccgtgt acaccacaat gtttggcggc gtgagctgga tgattagaat cctgatcggc    2220
ttcctggtgc tgtggatcgg caccaatagc cggaacacca gcatggccat gacctgcatc    2280
gccgtgggcg gcatcaccct gtttctgggc ttcaccgtgc aggcctga              2328

<210> SEQ ID NO 4
<211> LENGTH: 2325
<212> TYPE: DNA
<213> ORGANISM: Dengue virus

<400> SEQUENCE: 4
atgaacaacc aacggaaaaa gacgggtcga ccgtctttca atatgctgaa acgcgcgaga      60
aaccgcgtgt caactgtttc acagttggcg aagagattct caaaaggatt gctttcaggc     120
caaggaccca tgaaattggt gatggctttt atagcattcc taagatttct agccatacct     180
ccaacagcag gaattttggc tagatggggc tcattcaaga gaatggagc gatcaaagtg     240 ttacgggtt tcaagaaaga aatctcaaac atgttgaaca taatgaacag gaggaaaaga     300
tctgtgacca tgctcctcat gctgctgccc acagccctgg cgttccatct gaccacccga     360
gggggagagc cgcacatgat agttagcaag caggaaagag aaaatcact tttgtttaag     420 acctctgcag gtgtcaacat gtgcaccctt attgcaatgg atttgggaga gttatgtgag     480
gacacaatga cctacaaatg cccccggatc actgagacgg aaccagatga cgttgactgt     540
tggtgcaatg ccacggagac atgggtgacc tatggaacat gttctcaaac tggtgaacac     600
cgacgagaca acgttccgt cgcactggca ccacacgtag gcttggtct agaaacaaga     660 accgaaacgt ggatgtcctc tgaaggcgct tggaaacaaa tacaaaaagt ggagacctgg     720
gctctgagac acccaggatt cacggtgata gcccttttc tagcacatgc cataggaaca     780
tccatcaccc agaaagggat catttttatt ttgctgatgc tggtaactcc atccatggcc     840
atgcggtgcg tgggaatagg caacagagac ttcgtggaag actgtcagg agctacgtgg     900 gtggatgtgt tactggagca tggaagttgc gtcactacca tggcaaaaga caaaccaaca     960
ctggacattg aactcttgaa gacggaggtc acaaaccctg ccgtcctgcg caaactgtgc    1020
```

```
attgaagcta aaatatcaaa caccaccacc gattcgagat gtccaacaca aggagaagcc   1080
acgctggtgg aagaacagga cacgaacttt gtgtgtcgac gaacgttcgt ggacagaggc   1140
tggggcaatg gttgtgggct attcggaaaa ggtagcttaa taacgtgtgc taagtttaag   1200
tgtgtgacaa aactggaagg aaagatagtc caatatgaaa acttaaaata ttcagtgata   1260
gtcaccgtac acactggaga ccagcaccaa gttggaaatg agaccacaga acatggaaca   1320
actgcaacca taacacctca agctcccacg tcggaaatac agctgacaga ctacggagct   1380
ctaacattgg attgttcacc tagaacaggg ctagacttta tgagatggt gttgttgaca     1440 atggaaaaaa aatcatggct cgtccacaaa caatggtttc tagacttacc actgccttgg   1500
acctcggggg cttcaacatc caagagact tggaatagac aagacttgct ggtcacattt     1560
aagacagctc atgcaaaaaa gcaggaagta gtcgtactag gatcacaaga aggagcaatg   1620
cacactgcgt tgactggagc gacagaaatc caaacgtctg gaacgacaac aatttttgca   1680
ggacacctga aatgcagact aaaaatggat aaactgactt taaagggat gtcatatgta     1740 atgtgcacag ggtcattcaa gttagagaag gaagtggctg agacccagca tggaactgtt   1800
ctagtgcagg ttaaatacga aggaacagat gcaccatgca agatcccctt ctcgtcccaa   1860
gatgagaagg gagtaaccca gaatgggaga ttgataacag ccaaccccat agtcactgac   1920
aaagaaaaac cagtcaacat tgaagcggag ccacctttg gtgagagcta cattgtggta    1980
ggagcaggtg aaaaagcttt gaaactaagc tggttcaaga agggaagcag tataggaaaa   2040
atgtttgaag caactgcccg tgagcacga aggatggcca tcctgggaga cactgcatgg     2100
gacttcggtt ctataggagg ggtgttcacg tctgtgggaa aactgataca ccagattttt   2160
gggactgcgt atggagtttt gttcagcggt gtttcttgga ccatgaagat aggaataggg   2220
attctgctga catggctagg attaaactca aggagcacgt ccctttcaat gacgtgtatc   2280
gcagttggca tggtcacgct gtacctagga gtcatggttc aggcg                   2325
```

<210> SEQ ID NO 5
<211> LENGTH: 775
<212> TYPE: PRT
<213> ORGANISM: Dengue Virus

<400> SEQUENCE: 5

```
Met Asn Asn Gln Arg Lys Lys Thr Gly Arg Pro Ser Phe Asn Met Leu
1               5                   10                  15

Lys Arg Ala Arg Asn Arg Val Ser Thr Val Ser Gln Leu Ala Lys Arg
            20                  25                  30

Phe Ser Lys Gly Leu Leu Ser Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Ile Leu Ala Arg Trp Gly Ser Phe Lys Lys Asn Gly Ala Ile Lys Val
65                  70                  75                  80

Leu Arg Gly Phe Lys Lys Glu Ile Ser Asn Met Leu Asn Ile Met Asn
                85                  90                  95

Arg Arg Lys Arg Ser Val Thr Met Leu Leu Met Leu Leu Pro Thr Ala
            100                 105                 110

Leu Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140
```

```
Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Thr Glu Pro Asp
            165                 170                 175

Asp Val Asp Cys Trp Cys Asn Ala Thr Glu Thr Trp Val Thr Tyr Gly
        180                 185                 190

Thr Cys Ser Gln Thr Gly Glu His Arg Arg Asp Lys Arg Ser Val Ala
    195                 200                 205

Leu Ala Pro His Val Gly Leu Gly Leu Glu Thr Arg Thr Glu Thr Trp
210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Thr
        355                 360                 365

Asn Phe Val Cys Arg Arg Thr Phe Val Asp Arg Gly Trp Gly Asn Gly
370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Ala Leu Thr Leu Asp
450                 455                 460

Cys Ser Pro Arg Thr Gly Leu Asp Phe Asn Glu Met Val Leu Leu Thr
465                 470                 475                 480

Met Glu Lys Lys Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575
```

```
Met Ser Tyr Val Met Cys Thr Gly Ser Phe Lys Leu Glu Lys Glu Val
                580                 585                 590
Ala Glu Thr Gln His Gly Thr Val Leu Val Gln Val Lys Tyr Glu Gly
            595                 600                 605
Thr Asp Ala Pro Cys Lys Ile Pro Phe Ser Ser Gln Asp Glu Lys Gly
        610                 615                 620
Val Thr Gln Asn Gly Arg Leu Ile Thr Ala Asn Pro Ile Val Thr Asp
625                 630                 635                 640
Lys Glu Lys Pro Val Asn Ile Glu Ala Glu Pro Pro Phe Gly Glu Ser
                645                 650                 655
Tyr Ile Val Val Gly Ala Gly Glu Lys Ala Leu Lys Leu Ser Trp Phe
            660                 665                 670
Lys Lys Gly Ser Ser Ile Gly Lys Met Phe Glu Ala Thr Ala Arg Gly
        675                 680                 685
Ala Arg Arg Met Ala Ile Leu Gly Asp Thr Ala Trp Asp Phe Gly Ser
690                 695                 700
Ile Gly Gly Val Phe Thr Ser Val Gly Lys Leu Ile His Gln Ile Phe
705                 710                 715                 720
Gly Thr Ala Tyr Gly Val Leu Phe Ser Gly Val Ser Trp Thr Met Lys
                725                 730                 735
Ile Gly Ile Gly Ile Leu Leu Thr Trp Leu Gly Leu Asn Ser Arg Ser
            740                 745                 750
Thr Ser Leu Ser Met Thr Cys Ile Ala Val Gly Met Val Thr Leu Tyr
        755                 760                 765
Leu Gly Val Met Val Gln Ala
        770                 775

<210> SEQ ID NO 6
<211> LENGTH: 2328
<212> TYPE: DNA
<213> ORGANISM: Dengue Virus

<400> SEQUENCE: 6
atgaataacc aacggaaaaa ggcgaaaaac acgcctttca atatgctgaa acgcgagaga      60
aaccgcgtgt cgactgtgca acagctgaca aagagattct cacttggaat gctgcaggga     120
cgaggaccat taaaactgtt catggccctg gtggcgttcc ttcgtttcct aacaatccca     180
ccaacagcag ggatattgaa gagatgggga caattaaaa atcaaaagc tattaatgtt      240
ttgagagggt tcaggaaaga gattggaagg atgctgaaca tcttgaatag agacgcaga     300
tctgcaggca tgatcattat gctgattcca cagtgatgg cgttccattt aaccacacgt     360
aacggagaac cacacatgat cgtcagcaga aagagaaag ggaaaagtct tctgtttaaa     420
acagaggatg gcgtgaacat gtgtaccctc atggccatgg accttggtga attgtgtgaa     480
gacacaatca cgtacaagtg tccccttctc aggcagaatg agccagaaga catagactgt     540
tggtgcaact ctacgtccac gtgggtaact tatgggacgt gtaccaccat gggagaacat     600
agaagagaaa aaagatcagt ggcactcgtt ccacatgtgg aatgggact ggagacacga     660
actgaaacat ggatgtcatc agaagggc tggaaacatg tccagagaat gaaacttgg      720
atcttgagac atccaggctt caccatgatg cagcaatcc tggcatacac cataggaacg     780
acacatttcc aaagagccct gatttcatc ttactgacag ctgtcactcc ttcaatgaca     840
atgcgttgca taggaatgtc aaatagagac tttgtggaag gggtttcagg aggaagctgg     900
gttgacatag tcttagaaca tggaagctgt gtgacgacga tggcaaaaaa caaaccaaca     960
```

-continued

```
ttggattttg aactgataaa aacagaagcc aaacagcctg ccaccctaag gaagtactgt   1020
atagaggcaa agctaaccaa cacaacaaca gaatctcgct gcccaacaca aggggaaccc   1080
agcctaaatg aagagcagga caaaaggttc gtctgcaaac actccatggt agacagagga   1140
tggggaaatg gatgtggact atttggaaag ggaggcattg tgacctgtgc tatgttcaga   1200
tgcaaaaaga acatggaagg aaaagttgtg caaccagaaa acttggaata caccattgtg   1260
ataacacctc actcagggga agagcatgca gtcggaaatg acacaggaaa acatggcaag   1320
gaaatcaaaa taacaccaca gagttccatc acagaagcag aattgacagg ttatggcact   1380
gtcacaatgg agtgctctcc aagaacgggc ctcgacttca atgagatggt gttgttgcag   1440
atggaaaata aagcttggct ggtgcacagg caatggttcc tagacctgcc gttaccatgg   1500
ttgcccggag cggacacaca agggtcaaat tggatacaga aagagacatt ggtcactttc   1560
aaaaatcccc atgcgaagaa acaggatgtt gttgttttag gatcccaaga aggggccatg   1620
cacacagcac ttacaggggc cacagaaatc caaatgtcat caggaaactt actcttcaca   1680
ggacatctca agtgcaggct gagaatggac aagctacagc tcaaaggaat gtcatactct   1740
atgtgcacag gaaagtttaa agttgtgaag gaaatagcag aaacacaaca tggaacaata   1800
gttatcagag tgcaatatga aggggacggc tctccatgca agatcccttt tgagataatg   1860
gatttggaaa aaagacatgt cttaggtcgc ctgattacag tcaacccaat tgtgacagaa   1920
aaagatagcc cagtcaacat agaagcagaa cctccattcg gagacagcta catcatcata   1980
ggagtagagc cgggacaact gaagctcaac tggtttaaga aaggaagttc tatcggccaa   2040
atgtttgaga caacaatgag gggggcgaag agaatggcca ttttaggtga cacagcctgg   2100
gattttggat ccttgggagg agtgtttaca tctataggaa aggctctcca ccaagtcttt   2160
ggagcaatct atggagctgc cttcagtggg gtttcatgga ctatgaaaat cctcatagga   2220
gtcattatca catggatagg aatgaattca cgcagcacct cactgtctgt gacactagta   2280
ttggtgggaa ttgtgacact gtatttggga gtcatggtgc aggcctaa                2328
```

```

<210> SEQ ID NO 7
<211> LENGTH: 775
<212> TYPE: PRT
<213> ORGANISM: Dengue Virus

<400> SEQUENCE: 7

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140
```

```
Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
```

```
                565                 570                 575
Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
                740                 745                 750

Thr Ser Leu Ser Val Thr Leu Val Leu Val Gly Ile Val Thr Leu Tyr
            755                 760                 765

Leu Gly Val Met Val Gln Ala
    770                 775

<210> SEQ ID NO 8
<211> LENGTH: 2325
<212> TYPE: DNA
<213> ORGANISM: Dengue Virus

<400> SEQUENCE: 8
atgaaccaac gaaaaaggt ggttagacca ccttcaata tgctgaaacg cgagagaaac      60
cgcgtatcaa cccctcaagg gttggtgaag agattctcaa ccggactttt ttctgggaaa    120
ggacccttac ggatggtgct agcattcatc acgttttgc gagtcctttc catcccacca     180
acagcaggga ttctgaagag atggggacag ttgaagaaaa ataaggccat caagatactg    240
attggattca ggaaggagat aggccgcatg ctgaacatct tgaacgggag aaaaaggtca    300
acgataacat tgctgtgctt gattccacc gtaatggcgt tcacttgtc aacaagagat     360 ggcgaacccc tcatgatagt ggcaaaacat gaaaggggga gacctctctt gtttaagaca    420
acagagggga tcaacaaatg cactctcatt gccatggact gggtgaaat gtgtgaggac    480 actgtcacgt ataaatgccc cctactggtc aataccgaac tgaagacat tgattgctgg    540 tgcaacctca cgtctacctg ggtcatgtat gggacatgca cccagagcgg agaacggaga    600
cgagagaagc gctcagtagc tttaacacca cattcaggaa tgggattgga acaagagct    660 gagacatgga tgtcatcgga agggcttgg aagcatgctc agagagtaga gagctggata    720
ctcagaaacc caggattcgc gctcttggca ggatttatgg cttatatgat tgggcaaaca    780
ggaatccagc gaactgtctt ctttgtccta atgatgctgg tcgccccatc ctacggaatg    840
cgatgcgtag gagtaggaaa cagagacttt gtggaaggag tctcaggtgg agcatgggtc    900
gacctggtgc tagaacatgg aggatgcgtc acaaccatgg cccagggaaa accaaccttg    960
```

```
gattttgaac tgactaagac aacagccaag gaagtggctc tgttaagaac ctattgcatt    1020
gaagcctcaa tatcaaacat aactacggca acaagatgtc aacgcaagg agagccttat    1080
ctgaaagagg aacaggacca acagtacatt tgccggagag atgtggtaga cagagggtgg   1140
ggcaatggct gtggcctgtt tggaaaagga ggagttgtga catgtgcgaa gttttcatgt   1200
tcggggaaga taacaggcaa tttggtccaa attgagaacc tcgaatacac agtggttgta   1260
acagtccaca atggagacac ccatgcagta ggaaatgaca catccaatca tggagttaca   1320
gccatgataa ctcccaggtc accatcggtg gaagtcaaat gccggacta tggagaacta   1380
acactcgatt gtgaacccag gtctggaatt gactttaatg agatgattct gatgaaaatg   1440
aaaaagaaaa catggctcgt gcataagcaa tggttttttgg atctgcctct tccatggaca   1500
gcaggagcag acacatcaga ggttcactgg aattacaaag agaatggt gacatttaag    1560
gttcctcatg ccaagagaca ggatgtgaca gtgctgggat ctcaggaagg agccatgcat   1620
tctgccctcg ctggagccac agaagtggac tccggtgatg gaaatcacat gtttgcagga   1680
catctcaagt gcaaagtccg catggagaaa ttgagaatca agggaatgtc atacacgatg    1740
tgttcaggaa agttttcaat tgacaaagag atggcagaaa cacagcatgg gacaacagtg   1800
gtgaaagtca gtatgaagg tgctggagct ccgtgtaaag tccccataga gataagagat    1860
gtaaacaagg aaaagtggt tgggcgtatc atctcatcca ccctttggc tgagaatacc     1920
aacagtgtaa ccaacataga attagaaccc ccctttgggg acagctacat agtgataggt   1980
gttggaagca gcgcattaac actccattgg ttcaggaaag ggagttccat ggcaagatg    2040
tttgagtcca catacagagg tgcaaaacga atggccattc taggtgaaac agcttgggat   2100
tttggttccg ttggtggact gttcacatca ttgggaaagg ctgtgcacca ggtttttgga   2160
agtgtgtata caaccatgtt tggaggagtc tcatggatga ttagaatcct aattgggttc   2220
ttagtgttgt ggattggcac gaactcaagg aacacttcaa tggccatgac gtgcatagct   2280
gttggaggaa tcactctgtt tctgggcttc acagttcaag cataa                   2325

<210> SEQ ID NO 9
<211> LENGTH: 774
<212> TYPE: PRT
<213> ORGANISM: Dengue Virus

<400> SEQUENCE: 9

Met Asn Gln Arg Lys Lys Val Val Arg Pro Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Lys Ile Leu
65                  70                  75                  80

Ile Gly Phe Arg Lys Glu Ile Gly Arg Met Leu Asn Ile Leu Asn Gly
                85                  90                  95

Arg Lys Arg Ser Thr Ile Thr Leu Leu Cys Leu Ile Pro Thr Val Met
            100                 105                 110

Ala Phe His Leu Ser Thr Arg Asp Gly Glu Pro Leu Met Ile Val Ala
        115                 120                 125

Lys His Glu Arg Gly Arg Pro Leu Leu Phe Lys Thr Thr Glu Gly Ile
```

-continued

```
            130                 135                 140
Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                    165                 170                 175

Ile Asp Cys Trp Cys Asn Leu Thr Ser Thr Trp Val Met Tyr Gly Thr
                    180                 185                 190

Cys Thr Gln Ser Gly Glu Arg Arg Glu Lys Arg Ser Val Ala Leu
                195                 200                 205

Thr Pro His Ser Gly Met Gly Leu Glu Thr Arg Ala Glu Thr Trp Met
    210                 215                 220

Ser Ser Glu Gly Ala Trp Lys His Ala Gln Arg Val Glu Ser Trp Ile
225                 230                 235                 240

Leu Arg Asn Pro Gly Phe Ala Leu Leu Ala Gly Phe Met Ala Tyr Met
                    245                 250                 255

Ile Gly Gln Thr Gly Ile Gln Arg Thr Val Phe Phe Val Leu Met Met
                260                 265                 270

Leu Val Ala Pro Ser Tyr Gly Met Arg Cys Val Gly Val Gly Asn Arg
            275                 280                 285

Asp Phe Val Glu Gly Val Ser Gly Gly Ala Trp Val Asp Leu Val Leu
    290                 295                 300

Glu His Gly Gly Cys Val Thr Thr Met Ala Gln Gly Lys Pro Thr Leu
305                 310                 315                 320

Asp Phe Glu Leu Thr Lys Thr Thr Ala Lys Glu Val Ala Leu Leu Arg
                    325                 330                 335

Thr Tyr Cys Ile Glu Ala Ser Ile Ser Asn Ile Thr Thr Ala Thr Arg
                340                 345                 350

Cys Pro Thr Gln Gly Glu Pro Tyr Leu Lys Glu Glu Gln Asp Gln Gln
            355                 360                 365

Tyr Ile Cys Arg Arg Asp Val Val Asp Arg Gly Trp Gly Asn Gly Cys
        370                 375                 380

Gly Leu Phe Gly Lys Gly Gly Val Val Thr Cys Ala Lys Phe Ser Cys
385                 390                 395                 400

Ser Gly Lys Ile Thr Gly Asn Leu Val Gln Ile Glu Asn Leu Glu Tyr
                    405                 410                 415

Thr Val Val Val Thr Val His Asn Gly Asp Thr His Ala Val Gly Asn
                420                 425                 430

Asp Thr Ser Asn His Gly Val Thr Ala Met Ile Thr Pro Arg Ser Pro
            435                 440                 445

Ser Val Glu Val Lys Leu Pro Asp Tyr Gly Glu Leu Thr Leu Asp Cys
450                 455                 460

Glu Pro Arg Ser Gly Ile Asp Phe Asn Glu Met Ile Leu Met Lys Met
465                 470                 475                 480

Lys Lys Lys Thr Trp Leu Val His Lys Gln Trp Phe Leu Asp Leu Pro
                    485                 490                 495

Leu Pro Trp Thr Ala Gly Ala Asp Thr Ser Glu Val His Trp Asn Tyr
                500                 505                 510

Lys Glu Arg Met Val Thr Phe Lys Val Pro His Ala Lys Arg Gln Asp
            515                 520                 525

Val Thr Val Leu Gly Ser Gln Glu Gly Ala Met His Ser Ala Leu Ala
    530                 535                 540

Gly Ala Thr Glu Val Asp Ser Gly Asp Gly Asn His Met Phe Ala Gly
545                 550                 555                 560
```

-continued

His Leu Lys Cys Lys Val Arg Met Glu Lys Leu Arg Ile Lys Gly Met
                565                 570                 575

Ser Tyr Thr Met Cys Ser Gly Lys Phe Ser Ile Asp Lys Glu Met Ala
            580                 585                 590

Glu Thr Gln His Gly Thr Thr Val Val Lys Val Lys Tyr Glu Gly Ala
        595                 600                 605

Gly Ala Pro Cys Lys Val Pro Ile Glu Ile Arg Asp Val Asn Lys Glu
    610                 615                 620

Lys Val Val Gly Arg Ile Ile Ser Ser Thr Pro Leu Ala Glu Asn Thr
625                 630                 635                 640

Asn Ser Val Thr Asn Ile Glu Leu Glu Pro Pro Phe Gly Asp Ser Tyr
            645                 650                 655

Ile Val Ile Gly Val Gly Ser Ser Ala Leu Thr Leu His Trp Phe Arg
        660                 665                 670

Lys Gly Ser Ser Ile Gly Lys Met Phe Glu Ser Thr Tyr Arg Gly Ala
    675                 680                 685

Lys Arg Met Ala Ile Leu Gly Glu Thr Ala Trp Asp Phe Gly Ser Val
690                 695                 700

Gly Gly Leu Phe Thr Ser Leu Gly Lys Ala Val His Gln Val Phe Gly
705                 710                 715                 720

Ser Val Tyr Thr Thr Met Phe Gly Gly Val Ser Trp Met Ile Arg Ile
            725                 730                 735

Leu Ile Gly Phe Leu Val Leu Trp Ile Gly Thr Asn Ser Arg Asn Thr
        740                 745                 750

Ser Met Ala Met Thr Cys Ile Ala Val Gly Gly Ile Thr Leu Phe Leu
    755                 760                 765

Gly Phe Thr Val Gln Ala
    770

<210> SEQ ID NO 10
<211> LENGTH: 29
<212> TYPE: DNA
<213> ORGANISM: artificial sequence
<220> FEATURE:
<223> OTHER INFORMATION: primer

<400> SEQUENCE: 10
caccatgaat aaccaacgga aaaggcga                                    29

<210> SEQ ID NO 11
<211> LENGTH: 36
<212> TYPE: DNA
<213> ORGANISM: artificial sequence
<220> FEATURE:
<223> OTHER INFORMATION: primer

<400> SEQUENCE: 11
tttcactatt aggcctgcac catgactccc aaatac                           36

<210> SEQ ID NO 12
<211> LENGTH: 49
<212> TYPE: DNA
<213> ORGANISM: artificial sequence
<220> FEATURE:
<223> OTHER INFORMATION: primer

<400> SEQUENCE: 12
ggttgatggg cggccgccac catgaaccaa cgaaaaaagg tggttagac             49

<210> SEQ ID NO 13

```
<211> LENGTH: 44
<212> TYPE: DNA
<213> ORGANISM: artificial sequence
<220> FEATURE:
<223> OTHER INFORMATION: primer

<400> SEQUENCE: 13
ccctctagag cggccttatg cttgaactgt gaagcccaga aaca                        44

<210> SEQ ID NO 14
<211> LENGTH: 51
<212> TYPE: DNA
<213> ORGANISM: artificial sequence
<220> FEATURE:
<223> OTHER INFORMATION: primer

<400> SEQUENCE: 14
gcctccggac tctagcggcc gccaccatga ataaccaacg gaaaaggcg a                 51

<210> SEQ ID NO 15
<211> LENGTH: 57
<212> TYPE: DNA
<213> ORGANISM: artificial sequence
<220> FEATURE:
<223> OTHER INFORMATION: primer

<400> SEQUENCE: 15
cgtcgcatgc acgcgtcatg ccgcggatct gcgtctccta ttcaagatgt tcagcat         57

<210> SEQ ID NO 16
<211> LENGTH: 46
<212> TYPE: DNA
<213> ORGANISM: artificial sequence
<220> FEATURE:
<223> OTHER INFORMATION: primer

<400> SEQUENCE: 16
aggagacgca gatccagctt atgtctgatg atgatgctgc ctgcca                     46

<210> SEQ ID NO 17
<211> LENGTH: 42
<212> TYPE: DNA
<213> ORGANISM: artificial sequence
<220> FEATURE:
<223> OTHER INFORMATION: primer

<400> SEQUENCE: 17
tgcacgcgtc atgccctaag cggcctgcac cacggcgccg ag                         42

<210> SEQ ID NO 18
<211> LENGTH: 43
<212> TYPE: DNA
<213> ORGANISM: artificial sequence
<220> FEATURE:
<223> OTHER INFORMATION: primer

<400> SEQUENCE: 18
aggagacgca gatccacgat aacattgctg tgcttgattc cca                        43

<210> SEQ ID NO 19
<211> LENGTH: 44
<212> TYPE: DNA
<213> ORGANISM: artificial sequence
<220> FEATURE:
<223> OTHER INFORMATION: primer

<400> SEQUENCE: 19
```

```
tgcacgcgtc atgcctcagg cctgcacggt gaagcccaga aaca              44
```

```
<210> SEQ ID NO 20
<211> LENGTH: 43
<212> TYPE: DNA
<213> ORGANISM: artificial sequence
<220> FEATURE:
<223> OTHER INFORMATION: primer

<400> SEQUENCE: 20
aggagacgca gatccaccat cacactgctg tgcctgattc cca               43
```

```
<210> SEQ ID NO 21
<211> LENGTH: 44
<212> TYPE: DNA
<213> ORGANISM: artificial sequence
<220> FEATURE:
<223> OTHER INFORMATION: primer

<400> SEQUENCE: 21
tgcacgcgtc atgcctcagg cctgcacggt gaagcccaga aaca              44
```

```
<210> SEQ ID NO 22
<211> LENGTH: 2328
<212> TYPE: DNA
<213> ORGANISM: Dengue Virus

<400> SEQUENCE: 22
atgaataacc aacggaaaaa ggcgaaaaac acgcctttca atatgctgaa acgcgagaga    60
aaccgcgtgt cgactgtgca acagctgaca aagagattct cacttggaat gctgcaggga   120
cgaggaccat taaaactgtt catggccctg gtggcgttcc ttcgtttcct aacaatccca   180
ccaacagcag ggatattgaa gagatgggga acaattaaaa aatcaaaagc cattaatgtt   240
ttgagagggt tcaggaaaga gattggaagg atgctgaaca tcttgaatag agacgcaga    300
tctgcaggca tgatcattat gttgattcca acagtgatgg cgttccatct aaccacacgt   360
aacggagaac acacatgat cgtcagtaga caagagaaag ggaaaagtct tctgtttaaa   420
acagaggatg gtgtgaacat gtgcacccctc atggccatgg accttggtga attgtgtgaa   480
gacacaatca cgtataactg tccccttctc aggcagaatg agccagaaga catagactgt   540
tggtgcaact ccacgtccac atgggtaact tatgggacgt gtactaccac gggagaacat   600
agaagaggaa aaagatcagt ggcactcgtt ccacatgtgg aatgggact ggagacgcga   660
actgaaacat ggatgtcatc agaagggct tggaaacatg cccagagaat tgaaacttgg   720
atcctgagac atccaggctt caccataatg gcagcaatcc tggcatatac catagggacg   780
acacatttcc agagagccct gatttcatc ttactgacag ctgtcgctcc ttcaatgaca   840
atgcgttgca taggaatatc aaatagagac tttgtagaag gggttcagg gggaagctgg   900
gttgacatag tcttagaaca tggaagctgc gtgacgacga tggcaaaaaa caaaccaaca   960
ttggatttg aactgataaa aacagaagcc aaacagcctg ccaccctaag gaagtactgt  1020
atagaggcaa agctaaccaa cacaacaaca gaatctcgct gcccaacaca aggggaaccc  1080
agcctaaatg aagagcagga caaaaggttc gtctgcaaac actccatggt agacagagga  1140
tggggaaatg gatgtggatt gtttgggaag gaggcattg tgacctgtgc tatgtttaca  1200
tgcaaaaaga acatggaagg aaaagttgtg caaccagaaa acttggaata caccattgtg  1260
gtaacacctc actcagggga agagcatgcg gtcggaaatg acacaggaaa acatggcaag  1320
gaaatcaaag taacaccgca gagttccatc acagaagcag aattgacagg ctatggcact  1380
```

```
gtcacgatgg agtgctctcc gagaacaggc ctcgacttca atgagatggt gttgctgcag    1440
atgaaagaca aagcttggct ggtgcacagg caatggttcc tagacctgcc gttaccatgg    1500
ctgcccggag cggatacaca agggtcaaat tggatacaga agaaacatt  ggtcactttc    1560 aaaaatcccc atgcgaagaa acaggatgtt gttgttttag gatcccaaga aggggccatg    1620
cacacagcac tcagggggc  cacagaaatc caaatgtcat caggaaattt actcttcaca    1680
ggacatctca agtgcaggct gagaatggac aagctacagc tcaaaggaat gtcatactct    1740
atgtgcacag gaaagtttaa agttgtgaag gaaatagcag aaacacaaca tggaacaata    1800
gttatcagag tgcaatatga aggggacggc tctccatgta aaatcccttt tgagataatg    1860
gatttggaaa aagacatgt  cttaggtcgc ctgatcacag tcaacccaat tgtgacagaa    1920
aaagatagcc cagtcaacat agaagcagaa cctccattcg agacagcta  catcatcata    1980 ggagtagacc cgggacaact gaagctcaac tggtttaaga aggaagttc  tatcggccaa    2040 atgtttgaga caacaatgag gggggcgaag agaatggcca ttttgggtga cacagcctgg    2100
gattttggat ccctggggag agtgtttaca tctataggaa aagctctcca ccaagtcttt    2160
ggagcaatct atggagccgc cttcagtggg gtttcatgga ctatgaaaat cctcataggg    2220
gtcattatca catggatagg aatgaattca cgcagcacct cactgtctgt gtcactagta    2280
ttggtgggaa ttgtgacact gtatttggga gtcatggtgc aggcctaa              2328

<210> SEQ ID NO 23
<211> LENGTH: 775
<212> TYPE: PRT
<213> ORGANISM: Dengue Virus

<400> SEQUENCE: 23

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Asn Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Gly Lys Arg Ser Val Ala
        195                 200                 205

Leu Val Pro His Val Gly Met Gly Leu Glu Thr Arg Thr Glu Thr Trp
```

-continued

```
            210                 215                 220
Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                    245                 250                 255

Thr Ile Gly Thr Thr His Phe Gln Arg Ala Leu Ile Phe Ile Leu Leu
                260                 265                 270

Thr Ala Val Ala Pro Ser Met Thr Met Arg Cys Ile Gly Ile Ser Asn
            275                 280                 285

Arg Asp Phe Val Glu Gly Val Ser Gly Ser Trp Val Asp Ile Val
290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
                340                 345                 350

Arg Cys Pro Thr Gln Gly Glu Pro Ser Leu Asn Glu Glu Gln Asp Lys
                355                 360                 365

Arg Phe Val Cys Lys His Ser Met Val Asp Arg Gly Trp Gly Asn Gly
370                 375                 380

Cys Gly Leu Phe Gly Lys Gly Ile Val Thr Cys Ala Met Phe Thr
385                 390                 395                 400

Cys Lys Lys Asn Met Glu Gly Lys Val Val Gln Pro Glu Asn Leu Glu
                405                 410                 415

Tyr Thr Ile Val Val Thr Pro His Ser Gly Glu Glu His Ala Val Gly
                420                 425                 430

Asn Asp Thr Gly Lys His Gly Lys Glu Ile Lys Val Thr Pro Gln Ser
            435                 440                 445

Ser Ile Thr Glu Ala Glu Leu Thr Gly Tyr Gly Thr Val Thr Met Glu
450                 455                 460

Cys Ser Pro Arg Thr Gly Leu Asp Phe Asn Glu Met Val Leu Leu Gln
465                 470                 475                 480

Met Lys Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
                500                 505                 510

Gln Lys Glu Thr Leu Val Thr Phe Lys Asn Pro His Ala Lys Lys Gln
                515                 520                 525

Asp Val Val Val Leu Gly Ser Gln Glu Gly Ala Met His Thr Ala Leu
            530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
                595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640
```

```
Lys Asp Ser Pro Val Asn Ile Glu Ala Glu Pro Phe Gly Asp Ser
                645                 650                 655

Tyr Ile Ile Ile Gly Val Asp Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Ile Val Thr Leu Tyr
        755                 760                 765

Leu Gly Val Met Val Gln Ala
    770                 775

<210> SEQ ID NO 24
<211> LENGTH: 5
<212> TYPE: PRT
<213> ORGANISM: artificial sequence
<220> FEATURE:
<223> OTHER INFORMATION: cleavage sequence

<400> SEQUENCE: 24

Arg Arg Arg Arg Ser
1               5

<210> SEQ ID NO 25
<211> LENGTH: 5
<212> TYPE: PRT
<213> ORGANISM: artificial sequence
<220> FEATURE:
<223> OTHER INFORMATION: cleavage sequence

<400> SEQUENCE: 25

Arg Arg Lys Arg Ser
1               5

<210> SEQ ID NO 26
<211> LENGTH: 5
<212> TYPE: PRT
<213> ORGANISM: artificial sequence
<220> FEATURE:
<223> OTHER INFORMATION: cleavage sequence

<400> SEQUENCE: 26

Lys Arg Lys Lys Thr
1               5

<210> SEQ ID NO 27
<211> LENGTH: 5
<212> TYPE: PRT
<213> ORGANISM: artificial sequence
<220> FEATURE:
<223> OTHER INFORMATION: cleavage sequence

<400> SEQUENCE: 27

Gly Arg Lys Arg Ser
1               5
```

FLAVIVIRUS REPORTER VIRUS AND METHODS OF MAKING AND USING THE SAME

CROSS REFERENCE TO RELATED APPLICATIONS

This application claims priority to U.S. Provisional Application No. 61/259,279, filed Nov. 9, 2009, which is herein incorporated by reference in their entirety.

GOVERNMENT SUPPORT

This invention was made with U.S. Government support (NIH Grant No. AI062100) and the U.S. Government may therefore have certain rights in the invention.

BACKGROUND OF THE INVENTION

Flaviviruses have a global impact due to their widespread distribution and ability to cause encephalitis in humans and economically important domesticated animals. Of the approximately seventy viruses in the genus, roughly half have been associated with human disease. Several members of this group, such as dengue virus (DENV) and West Nile virus (WNV), are considered emerging or re-emerging pathogens because the incidence with which they encounter humans and cause disease is increasing each year at an alarming rate. Globally, DENV has become the most significant source of arthropod-borne viral disease in humans. Approximately 2.5 billion people (40% of the world's population) live at risk for DENV exposure across the globe, resulting in more than 100 million cases of DENV related illnesses each year.

The genome of flaviviruses such as DENV is a positive-stranded RNA. In the presence of non-structural proteins encoded by the virus, the RNA can be replicated within the cytoplasm of a host cell. A nucleic acid molecule that codes for all the proteins necessary for its replication in a cell is termed a "replicon". If RNA encoding the DENV replicon is transfected into cells, the replicon can replicate. RNA-based replicons of Kunjin virus that carry a reporter gene have been described (Khromykh, et al. (1998), J Virol, 72:5967-77, Khromykh, et al. (1997), J Virol, 71:1497-505, Varnayski, et al. (1999), Virology, 255:366-75, Westaway, et al. (2005)) (U.S. Pat. No. 6,893,866). Such replicons can be transfected into stable or inducible cell lines to produce reporter viruses (Harvey, et al. (2004), J Virol, 78:531-8). Subgenomic replicons of Dengue virus have also been described (Holden, et al. (2006), Virology, 344:439-52) (Pang, et al. (2003);U.S. Patent Publication No. 2004/0265338)). A plasmid carrying a DNA-based version of a replicon that could be transfected into a cell directly (rather than an RNA transcript from the DNA) has been described for West Nile virus (Pierson, et al. (2005), Virology, 334:28-40). Replication-competent clones of West Nile virus have also been described that carry a green fluorescent protein (GFP) reporter virus (Pierson, et al. (2005), Virology, 334:28-40).

Four different serotypes of DENV are transmitted to humans through the bite of *Aedes aegypti* and *Aedes albopictus* mosquitoes. Clinical manifestations of exposure to DENV vary significantly (for review see (Gibbons, et al. (2002), Bmj, 324:1563-6)). Common clinical manifestations of dengue fever (DF) include a febrile illness accompanied by retroorbital, muscle and joint pain. While primary exposure to DENV is not associated with significant mortality, a small percentage of exposed individuals experience a more severe disease course referred to as dengue hemorrhagic fever (DHF). DHF, which is fatal in up to 10% of affected individuals, is most common in individuals that are sequentially infected with multiple different serotypes of the virus. Of significant concern is the rapid increase in the number of DHF cases during the past twenty years, resulting in over 450,000 cases of DHF each year (Monath, et al. (1996), Fields Virology, 2:961-1034). The increasingly common spread of different dengue serotypes is expected to increase the frequency of DHF significantly.

Dengue viruses are small spherical virions composed of three viral structural proteins, a lipid envelope, and a copy of the RNA genome (Kuhn, et al. (2002), Cell, 108:717-25, Mukhopadhyay, et al. (2003), Science, 302:248, Zhang, et al. (2003), Embo J, 22:2604-13). The cell biology of DENV entry into cells is poorly understood. To date, a cellular receptor for DENV has not yet been identified, although recent evidence suggests a role for DC-SIGN and/or DC-SIGNR during attachment and entry into primary dendritic cells (Navarro-Sanchez, et al. (2003), EMBO Rep, 4:723-8, Tassaneetrithep, et al. (2003), J Exp Med, 197:823-9). The role of the receptor is to bind virus particles on the cell surface and deliver them into the mildly acidic endosomal compartments of the cell, where the envelope proteins of the virus mediate fusion in a pH-dependent fashion.

The positive sense RNA genome of DENV is approximately 11 kb in length and encodes a single polyprotein that is cleaved by cellular and viral proteases into ten smaller functional subunits: three structural and seven non-structural (NS) proteins (Khromykh, et al. (1999), J Virol, 73:10272-80, Khromykh, et al. (2000), J Virol, 74:3253-63, Rice (1996), Fields Virology, 2:931-959). The structural proteins of DEN, which include the capsid, pre-membrane (prM) and envelope (E) proteins, are synthesized at the amino-terminus of the polyprotein and are present in the mature virus particle. The seven non-structural proteins encode all the enzymatic functions required for replication of the DENV genomic RNA, including a RNA-dependent RNA polymerase (NS5) (Rice (1996), Fields Virology, 2:931-959). The sequence encoding the DENV polyprotein is flanked by two untranslated regions (UTRs) that are required for efficient translation and genomic RNA replication (Khromykh, et al. (2003), J Virol, 77:10623-9, Khromykh, et al. (2000), J Virol, 74:3253-63, Novak, et al. (1994), Genes Dev, 8:1726-37). DENV RNA replication occurs in the cytoplasm at specialized virus-induced membrane structures (Mackenzie, et al. (1999), J Virol, 73:9555-67, Mackenzie, et al. (1998), Virology, 245:203-15). Viral particle biogenesis and budding occurs at the endoplasmic reticulum, and viruses are released through the secretory pathway of the cell (Lorenz, et al. (2003), J Virol, 77:4370-82, Mackenzie, et al. (2001), J Virol, 75:10787-99).

The ability of enveloped viruses to enter permissive cells is conferred by envelope glycoproteins incorporated into the viral membrane. Class II envelope proteins, encoded by the alpha- and flaviviruses, describe those that contain an internal fusion loop, lie flat across the surface of the native virion as dimers, and do not appear to form coiled-coils while mediating lipid mixing and fusion (reviewed in (Heinz, et al. (2000), Adv Virus Res, 55:231-69)). Like other class II fusion systems, DENV entry and fusion involves two separate proteins. The E protein plays a central role in virus entry by virtue of its capacity to bind receptor and mediate fusion in a pH-dependent fashion. The primary role of the second protein, prM, involves protecting newly formed particles from irreversible premature inactivation as they transit through mildly acidic compartments in the secretory pathway (Zhang, et al. (2003), Embo J, 22:2604-13). Other functions of prM have been demonstrated including directing E protein folding and trafficking (Lorenz, et al. (2002), J Virol, 76:5480-91). Structural studies suggest that all class II fusion proteins share a common structural design.

DENV virions are small spherical particles (50 nM) comprised of a lipid envelope incorporating 180 E glycoproteins arranged in a herringbone configuration (Kuhn, et al. (2002), Cell, 108:717-25). The capsid, prM and E components assemble at the endoplasmic reticulum to form an immature particle that buds into the lumen of the ER. Cleavage of the prM protein by the furin protease during trafficking to the cell surface (to generate the M protein), activates the fusion potential of the E protein, allowing the conformational changes that mediate fusion to occur upon exposure to low pH (Elshuber, et al. (2003), J Gen Virol, 84:183-91). Interestingly, expression of prM-E alone is sufficient for the production and secretion of subviral particles (SVPs) that, despite being smaller than mature viruses, retain the ability to mediate fusion in a manner analogous to mature particles containing capsid (Corver, et al. (2000), Virology, 269:37-46, Ferlenghi, et al. (2001), Mol Cell, 7:593-602, Heinz, et al. (1995), Vaccine, 13:1636-42). The ability to form subviral particles in the absence of any other viral proteins suggests that the forces that drive the process of particle biogenesis and budding reside in prM-E. Mature Dengue virus particles are approximately 50 nM in diameter and contain multiple copies of the viral capsid and the viral genomic RNA. Smaller 30 nM particles composed of prM-E proteins, called subviral particles, are also produced during virus infection. While subviral particles do not contain RNA or capsid, the E proteins on these particles are able to mediate receptor binding and fusion.

A primary target for neutralizing antibodies in a flavivirus infected host is the E glycoprotein present on the surface of the virus particle (Monath, et al. (1996), Fields Virology, 2:961-1034). Additionally, antibodies generated against prM and nonstructural protein-1 (NS1) have also been observed. Several lines of evidence support a significant role for such antibodies during virus clearance and the establishment of immunity following vaccination. For example, passive transfer of antibodies has been shown to confer protection in experimental systems with several flaviviruses, including tick bourne encephalitis (TBE), yellow fever virus (YF), Japanese encephalitis virus (JEV), WNV, and Saint Louis encephalitis virus (SLE). Studies in murine and hamster systems of WNV infection have reached similar conclusions. Several vaccine approaches are being developed, including the use of inactivated virus particles, live attenuated viruses, non-infectious subviral particles, subunit, and nucleic acid vaccines (Pugachev, et al. (2003), Int J Parasitol, 33:567-82). In many of these studies, particularly those in humans, the development of neutralizing antibodies is employed as a correlate of immunity and a measure of efficacy.

The development of a vaccine for DENV has been a significant challenge and the focus of considerable effort (Monath, et al. (1996), Fields Virology, 2:961-1034). While antibodies play a significant role in DENV immunity, the presence of DENV antibodies has also been linked to a more severe clinical outcome due to the ability of antibodies to facilitate DENV infection under some circumstances. While natural infection with one serotype of DENV results in generation of humoral immunity that protects against subsequent challenge with a homotypic virus, protection against other serotypes is transient. In fact, sequential exposure to different serotypes of DENV increases the likelihood of developing DHF. Pioneering work by Halstead and colleagues suggest that the presence of antibodies raised against the first serotype of DENV significantly impacts the outcome of a second exposure by allowing antibody dependent enhancement (ADE) of infection and the activation of both complement and the cellular immune system (Halstead (1988), Science, 239:476-81, Halstead (1989), Rev Infect Dis, 11 Suppl 4:S830-9, Halstead, et al. (1970), Yale J Biol Med, 42:311-28, Halstead, et al. (1977), J Exp Med, 146:201-17, Kliks, et al. (1989), Am J Trop Med Hyg, 40:444-51, Mongkolsapaya, et al. (2003), Nat Med, 9:921-7). Together, ADE has been linked to an increase in viral burden, increased vascular permeability, and a more severe disease course. One implication of these studies is that great care must be taken in the design of a vaccine against DENV to avoid a strategy that confers protection to only one serotype. Protection against only a single DENV serotype would increase the likelihood of an individual's chance of developing DHF should they encounter a second serotype of DENV. A tetravalent vaccine that simultaneously protects against all four serotypes of DENV is needed. Thus, characterizing not only the magnitude, but also the breadth, persistence, and specificity of the humoral response in response to vaccination is an important component of evaluating candidate vaccines and understanding pathogenesis in naturally infected individuals.

The standard method for detecting neutralizing antibodies to DENV is the plaque reduction neutralization test (PRNT) (Monath, et al. (1996), Fields Virology, 2:961-1034, Russell, et al. (1967), J Immunol, 99:291-6). Using this approach, the ability of an antibody to bind virus and neutralize its infectivity is measured as a reduction in the number of plaques formed following infection and subsequent propagation in cell culture. The PRNT approach involves the use of live infectious virus, and requires about a week for plaque formation and analysis. The quantitative power of plaque assays is limited by the number of wells examined and the number of plaques counted by the investigator. The latter process is somewhat subjective when plaque size and morphology is variable. The ability of flaviviruses to form plaques in infected cell monolayers is cell type-, and virus strain-dependent. Thus, the PRNT approach does not allow for the neutralizing capacity of antibodies to be detected using strains that plaque poorly, or on all permissive cell types, excluding many that may be relevant in vivo.

There is a need for better methods and compositions for the generation of pharmaceuticals and vaccines against flaviviruses, such as Dengue. The present invention fulfills these needs as well as others.

SUMMARY OF THE INVENTION

In some embodiments, the present invention provides isolated nucleic acid molecules comprising a nucleic acid sequence encoding a flavivirus capsid polypeptide and a nucleic acid sequence encoding a flavivirus prME polypeptide. In some embodiments, the nucleic acid sequence encoding the capsid is not codon optimized for protein expression. In some embodiments, the nucleic acid sequence encoding the prME polypeptide is codon optimized for protein expression. In some embodiments, the capsid and prME polypeptides are expressed as a single polypeptide.

In some embodiments, the present invention provides expression constructs comprising the nucleic acid molecules described herein. In some embodiments, the expression construct is a plasmid or a virus.

In some embodiments, the present invention provides cells comprising the nucleic acid molecules described herein and a flavivirus replicon. In some embodiments, the nucleic acid sequence encoding the capsid polypeptide and the replicon are from the same serotype. In some embodiments, the nucleic acid molecule encodes a cleavage site between the sequences encoding for the capsid polypeptide and prME polypeptide, wherein the sequence encoding the cleavage site is the same serotype as the nucleic acid sequence of said replicon.

In some embodiments, the present invention provides nucleic acid molecules comprising a first nucleic acid sequence encoding a flavivirus capsid polypeptide and a second nucleic acid sequence encoding a flavivirus prME polypeptide, wherein the first and second nucleic acid sequences are from different serotypes. In some embodiments, the present invention provides cells comprising a nucleic acid molecule encoding a flavivirus replicon and the nucleic acid molecules described herein, wherein the serotype of the nucleic acid molecule encoding the replicon is the same serotype as the nucleic acid molecule encoding the capsid polypeptide.

The present invention also provides for flavivirus particles. In some embodiments, the particles comprise a reporter comprising polypeptides encoded by a nucleic acid molecule of described herein.

The present invention also provides methods of generating an antibody against a flavivirus.

The present invention, in some embodiments, provides methods of identifying an inhibitor of flavivirus infection and/or replication.

BRIEF DESCRIPTION OF THE DRAWINGS

FIG. 1. Description of constructs used for Dengue RVP production. (A) Schematic of DENV CprME expression constructs used for production of RVPs. Solid colors indicate wild type sequences. Bars with diagonal stripes indicate codon optimized sequences. (B) Amino acid alignment of the NS3 cleavage site between Capsid and prM proteins of different Dengue serotypes and recombinant chimeras. Amino acid conservation is depicted in gray. Cleavage occurs between a dibasic sequence (e.g. "RR") at the P2 and P1 positions, and a mildly acidic residue (e.g. "S") in the P1' position.

FIG. 3. RVP production using the DENV2/3opt chimera. BHK21-clone 15 cells, carrying a stable DENV2 GFP replicon, were transfected with the indicated DENV expression constructs. Supernatants harvested and filtered at 48 hours post transfection were used to infect Raji-DC-SIGN-R or Raji DC-SIGN cell lines. Infections were allowed to progress for 72 hours at 37° C. Subsequently, cells were fixed and analyzed for GFP expression by flow cytometry. The percent infection using RVPs produced by transfection of the indicated plasmids is shown above. Surprisingly, it was found that DENV3opt CprME did not support RVP production. However, upon chimerization of a wild type (non-codon optimized) DENV2 Capsid with codon optimized prME DENV3 (DENV2/3opt), production of infectious RVPs was observed.

Figure 4:
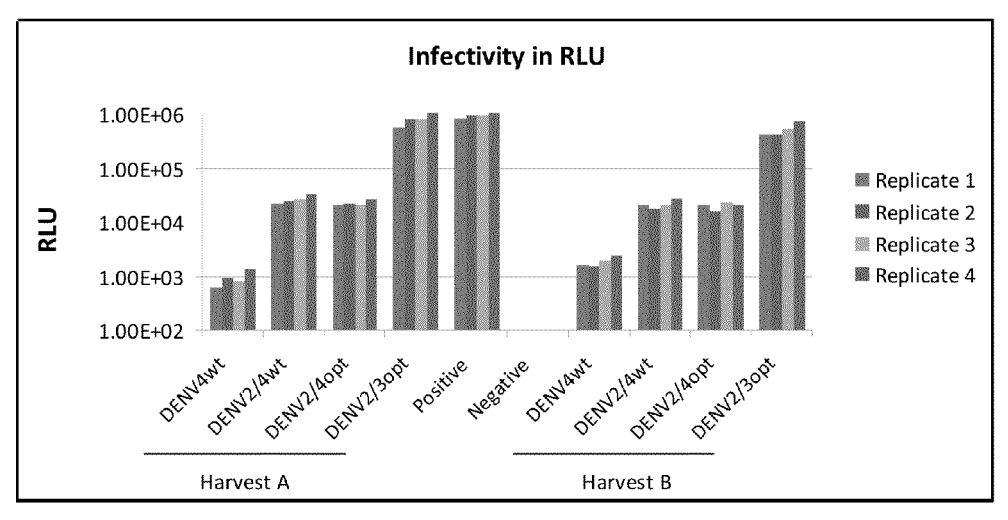

FIG. 4. RVPs produced using DENV2/DENV4 chimeras lead to increased infectivity of BHK-DC SIGN cells compared to DENV4 WT. Dengue RVPs were generated by transfecting BHK21-clone 15 cells containing a stable DENV2 Luciferase replicon with the CprME constructs indicated. Dengue RVPs carrying the luciferase reporter were harvested and used to infect target BHK-DC SIGN cells. 72 hours after infection, cells were lysed and assayed for luminescence. Infections were done in quadruplicate. For the negative control, BHK-DC SIGN cells were treated with supernatants from a mock-transfected BHK21-clone 15 cell line containing stable DENV2 Luciferase replicon. For the positive control, previously validated RVPs were used. RVPs produced using DENV2/4 chimeras demonstrate greater infectivity compared to DENV4 wt. However, codon optimization of DENV4 prME in the context of the DENV2/4 chimera did not further enhance infectivity, demonstrating that codon optimization of prME does not necessarily always result in greater numbers of infectious particles, even if it results in greater protein expression.

FIG. 6. Codon optimization in combination with chimerization results in increased DENV4 RVP infectivity. RVPs expressing GFP were produced by transfection of a GFP replicon in Trex cells conditionally expressing DENV4 wt, DENV2/4 wt, and DENV2/4opt structural proteins. Raji-DC-SIGN cells were infected with equal volumes of RVPs and analyzed for GFP expression by fluorescence microscopy 72 hours post infection. RVPs produced from the DENV2/4 wt chimera show a very small increase in infectivity over those produced using DENV4 wt, demonstrating that expression of the chimera itself in the absence of codon optimization is not sufficient for increased infectivity. RVPs produced from the DENV2/4 codon optimized chimera show increased infectivity compared to those produced from the DENV2/4 wt. This result emphasizes the requirement for a codon optimized chimera (containing a wild type Capsid and a codon-optimized prME) for maximal production of pseudoinfectious particles.

DETAILED DESCRIPTION

Figure 2:
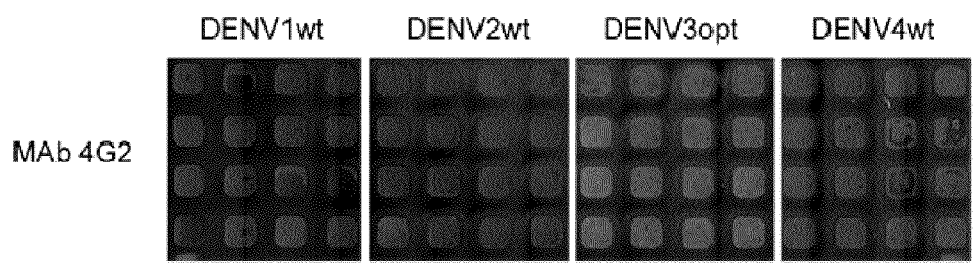
FIG. 2. Codon optimization of DENV3 leads to enhanced expression of Dengue structural proteins. Immunofluorescence staining of HEK-293T cells transfected with DENV expression plasmids. Cells transfected with the codon optimized DENV3 construct (DENV3opt) exhibit bright staining with the 4G2 monoclonal antibody while cells expressing DENV1, DENV2, and DENV4 exhibit faint staining. Each box contains 16 transfection replicates with the indicated construct.
Figure 5:
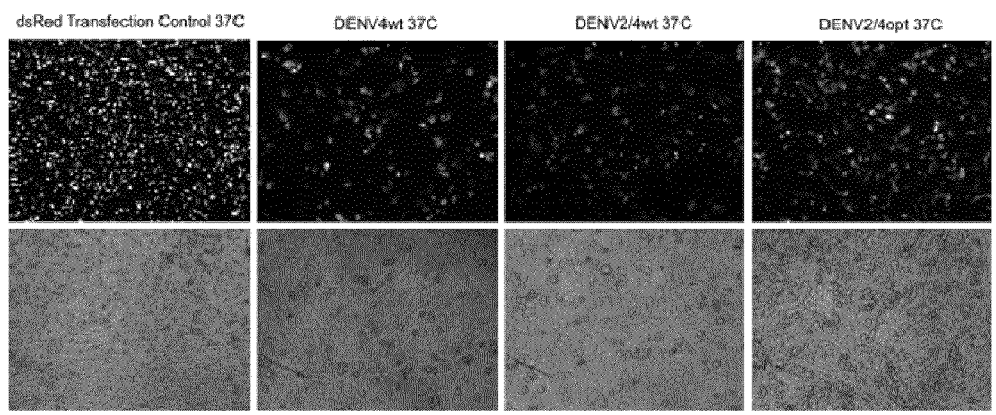
FIG. 5. Codon optimization of the DENV2/4 chimera results in high level expression of Dengue structural proteins in 293 TRex cells. 293 Trex cells conditionally expressing CprME proteins of Dengue serotype 4, the chimera DENV2/4 wt and the codon optimized chimera DENV2/4opt were treated with doxycycline for 36 hours followed by fixation and immunofluorescence staining with the monoclonal antibody 4G2. No difference in expression was detected between cells expressing DENV4 wt and those expressing the DENV2/4 wt chimera. In contrast, cells expressing the codon-optimized chimera, DENV2/4opt, exhibited increased expression levels of CprME proteins. Taken together, these results demonstrate that codon optimization for DENV4 prME sequence results in enhanced expression of viral proteins. Additionally, expression of the codon optimized chimera is better tolerated in Trex cells as demonstrated by an increase in cell density under this transfection condition.
Figure 7:
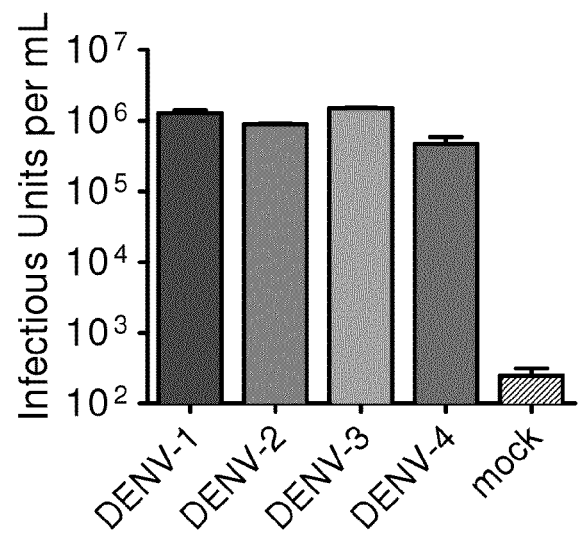
FIG. 7. Production and neutralization of dengue RVPs. A. DENV RVPs specific for all four serotypes were produced and used to infect Raji-DC-SIGNR cells. Infection was quantified at 48 hours by flow cytometry for GFP expression and infectious titer was calculated. B. Sera from naturally infected patients and vaccinated individuals were tested for neutralization against all four serotypes of DENV (DENV4 strain TVP shown). Values are normalized to infection levels observed in the absence of serum. All data is the mean of duplicate data points.
Figure 7:
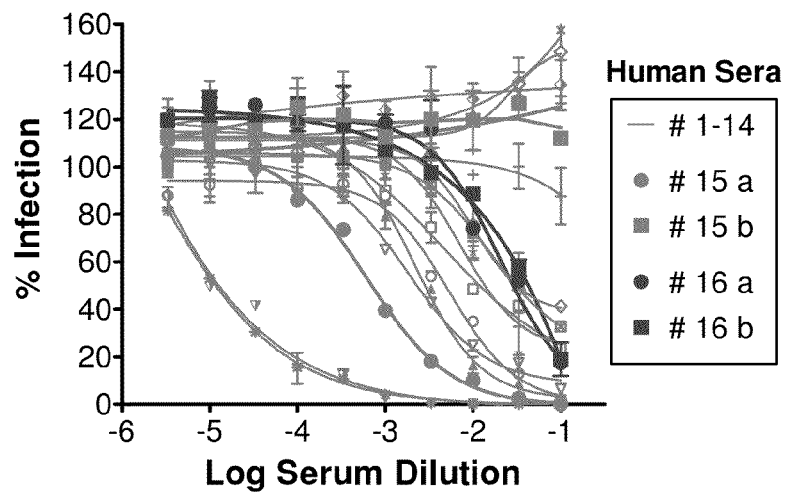
Figure 8:
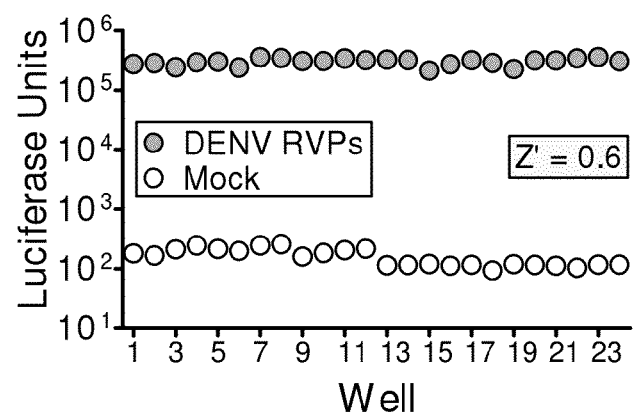
FIG. 8. DENV RVPs and the DENV reporter replicon can be used in HTS screens. A. DENV RVPs were used to infect BHK-DC-SIGN cells in 384-well format. Infection was quantified at 48 hours by measuring luciferase expression. B. Cells expressing a stable GFP reporter replicon were seeded in 384-wells and cultured for 48-72 hours with diverse compounds from a small molecule library (printed in quadruplicate, error bars are standard deviation) and measured for a loss of GFP expression in the absence of cytotoxicity. Positive 'hits' are highlighted in red (arrows).
Figure 8:
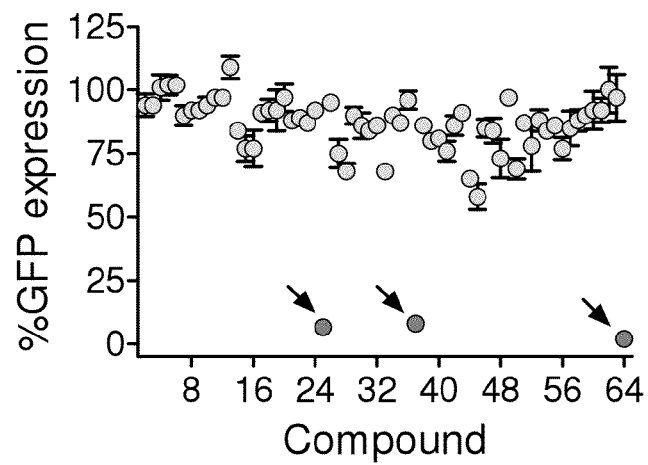

As discussed herein, the present invention describes the surprising and unexpected result that the optimization of the expression of certain proteins of a flavivirus does not lead to an increase in infectious viral production and can actually inhibit the production of infectious particle production. In contrast to the expected result, selectively optimizing the expression of certain proteins, while not optimizing the expression of other proteins unexpectedly and surprisingly leads to an increase in infectious viral particle production. The present application describes in some embodiments where selective optimization and, in some embodiments, chimerization of different strains or serotypes of a flavivirus, leads to an increase in infectious viral particle production.

The present application refers to flaviviruses. Examples of flaviviruses include, but are not limited to, Dengue, Japanese Encephalitis virus, West Nile Virus, Yellow Fever Virus, Tick-borne Encephalitis Virus, and the like. Additional examples of flaviviruses include, but are not limited to, Gadgets Gully virus (GGYV), Kadam virus (KADV), Kyasanur Forest disease virus (KFDV), Langat virus (LGTV), Omsk hemorrhagic fever virus (OHFV), Powassan virus (POWV), Royal Farm virus (RFV), Tick-borne encephalitis virus (TBEV), Louping ill virus (LIV), Meaban virus (MEAV), Saumarez Reef virus (SREV), Tyuleniy virus (TYUV), Aroa virus (AROAV), Dengue virus (DENV), Kedougou virus (KEDV), Japanese encephalitis virus group, Cacipacore virus (CPCV), Koutango virus (KOUV), Japanese encephalitis virus (JEV), Murray Valley encephalitis virus (MVEV), St. Louis encephalitis virus (SLEV), Usutu virus (USUV), West Nile virus (WNV), Kunjin virus, Yaounde virus (YAOV), Kokobera virus (KOKV), Ntaya virus group, Bagaza virus (BAGV), Ilheus virus (ILHV), Israel turkey meningoencephalomyelitis virus (ITV), Ntaya virus (NTAV), Tembusu virus (TMUV), Zika virus (ZIKV), Banzi virus (BANV), Bouboui virus (BOUV), Edge Hill virus (EHV), Jugra virus (JUGV), Saboya virus (SABV), Sepik virus (SEPV), Uganda S virus (UGSV), Wesselsbron virus (WESSV), Yellow fever virus (YFV), Entebbe bat virus (ENTV), Yokose virus (YOKV), Apoi virus (APOIV), Cowbone Ridge virus (CRV), Jutiapa virus (JUTV), Modoc virus (MODV), Sal Vieja virus (SVV), San Perlita virus (SPV), Rio Bravo virus group, Bukalasa bat virus (BBV), Carey Island virus (CIV), Dakar bat virus (DBV), Montana myotis leukoencephalitis virus (MMLV), Phnom Penh bat virus (PPBV), and Rio Bravo virus (RBV).

Many flavivirus can also include different serotypes. For example, Dengue virus has at least four known serotypes, which include, but are not limited to, DENV1, DENV2, DENV3, and DENV4. Any combination of flaviviruses and serotypes can be used as it is applies to the compositions (e.g. nucleic acid sequences, amino acid sequences, cleavage sequences, flavivirus proteins, and the like) and methods described herein. In some embodiments the combination of different flaviviruses is combined with the optimized and/or non-optimized nucleic acid sequences encoding the capsid polypeptide and/or the prM/E polypeptide. For example, in some embodiments, the capsid of other flaviviruses, such as Japanese Encephalitis virus, West Nile Virus, and Yellow Fever Virus can be used to support DENV RVP production. For example, a chimera of West Nile Virus Capsid and DENV prME can be used. In some embodiments, the chimera is used where the capsid is matched with the replicon and/or the NS3 protein. Matched means that the capsid, the replicon, cleavage site between Capsid and prME, and/or the NS3 protein are from the same flavivirus.

The nucleic acid sequences described herein can also be included in genetic constructs, nucleic acid constructs, or expression constructs. As used herein, the terms "genetic construct," "nucleic acid construct," and "expression construct" are used interchangeably and refer to the DNA or RNA molecules that comprise a nucleotide sequence which encodes one or more proteins. The coding sequence, or "encoding nucleic acid sequence," includes initiation and termination signals operably linked to regulatory elements including a promoter and polyadenylation signal capable of directing expression in a host cell or a cell of an individual to whom the nucleic acid molecule is administered.

As used herein, the term "expressible form" refers to nucleic acid constructs that contain the necessary regulatory elements operably linked to a coding sequence that encodes a protein such that when present in a host cell, the coding sequence will be expressed.

As used herein, the phrase "free from an entire Flavivirus genome" used in reference to a nucleic acid encoding a capsid protein or prME protein, or fragment thereof, indicates that the nucleic acid is in a form that is in a recombinant form or construct, or that it is otherwise isolated from its natural state in a Flavivirus genome. The nucleic acid sequences described herein can, in some embodiments, be free from an entire Flavivirus genome.

In some embodiments, the present invention provides a nucleic acid sequence encoding a replicon of a flavivirus. In some embodiments, a nucleic acid sequence encoding a replicon of the flavivirus comprises the minimal portion of the flavivirus genome capable of self-replication. In some embodiments, the nucleic acid sequence encoding a replicon comprises only the minimal portion of the flavivirus genome capable of self-replication. In some embodiments, the minimal portion does not include the structural proteins of the flavivirus. In some embodiments, the minimal portion comprises a nucleic acid sequence encoding the non-structural proteins of the flavivirus. The nucleic acid molecule can be either DNA or RNA. In some embodiments, the nucleic acid sequence is free of RNA bases. In some embodiments, the DNA encoding the replicon is a plasmid. In some embodiments, the DNA is free of a virus or is not packaged in a virus.

Any replicon can be used. A nucleic acid molecule that codes for all the proteins necessary for its replication in a cell is termed a "replicon". The replicon can be any replicon including, but not limited to the replicons described in Khromykh, et al. (1998), J Virol, 72:5967-77, Khromykh, et al. (1997), J Virol, 71:1497-505, Varnayski, et al. (1999), Virology, 255:366-75, Westaway, et al. (2005)) (U.S. Pat. No. 6,893,866), (Harvey, et al. (2004), J Virol, 78:531-8), and the like. Other replicons include subgenomic replicons of Dengue virus which have also been described in (Holden, et al. (2006), Virology, 344:439-52)(Pang, et al. (2003)) (U.S. Patent Application No. 2004/0265338). Other types of replicons can also be used including, but not limited to, a plasmid carrying a DNA-based version of a replicon that could be transfected into a cell directly (rather than an RNA transcript from the DNA) has been described for West Nile virus (Pierson, et al. (2005), Virology). Replication-competent clones of West Nile virus have also been described that carry a green fluorescent protein (GFP) reporter virus (Pierson, et al. (2005), Virology, 334:28-40). In some embodiments, the DENV replicon is the replicon described and used in Ansarah-Sobrinho, C., Nelson, S., Jost, C. A., Whitehead, S. S., and Pierson, T. C. (2008), "Temperature-dependent production of pseudoinfectious dengue reporter virus particles by complementation, Virology 381, 67-74. In some embodiments, the replicon is a DENV2 replicon. In some embodiments, the replicon is a DENV1, DENV3, or a DENV4 replicon. Each of the references describing the replicons are hereby incorporated by reference in its entirety, including but not limited to, the compositions comprising replicons and how to make the replicons.

The nucleic acid sequences described herein and throughout can comprise a promoter operably linked to the nucleic acid sequence encoding one or more proteins. The proteins can be, but not limited to, C, prME and/or the replicon of the flavivirus. The promoter can be any promoter, including but not limited to promoters that are functional in eukaryotic cells. In some embodiments, the promoter is specifically functional in a eukaryotic cell. In some embodiments, the promoter is, but not limited to a CMV promoter, SV40, and the like. In some embodiments, the promoter is an inducible promoter.

The nucleic acid sequence encoding replicons and the resulting replicons of the present invention can also comprise reporter constructs such that one can monitor the replication or expression of the genes found in the nucleic acid sequence of the replicon. The reporter can also be used to measure infectivity of any virus or virus-like particle that contains the replicon. Examples of reporters include, but are not limited to, a fluorescent reporter or an enzymatic reporter. Examples of enzymatic reporters include, but are not limited to, a luciferase reporter, β-Galactosidase reporter, alkaline phosphatase reporter, chloramphenicol acetyltransferase (CAT), and the like. Examples of fluorescent reporters include, but are not limited to, GFP (green fluorescent protein) reporter, RFP (red fluorescent protein) reporter, YFP (yellow fluorescent protein) reporter, nsTGP, and the like. Examples of luciferase reporters include, but are not limited to renilla luciferase reporter and firefly luciferase reporter. In some embodiments the replicon comprises a gene that allows for selection of a cell that comprises the replicon. For example, a cell can be selected for comprising the nucleic acid sequence encoding the replicon by contacting the cell with a drug or chemical that because of the presence of the replicon the cell is resistant to the drug or chemical whereas cells that do not contain the replicon will die. Accordingly, in some embodiments, the nucleic acid sequence encoding the replicon comprises a drug resistant gene that allows a cell to escape the effects of drug or chemical. Examples of markers that can be used include, but are not limited to, zeomycin, and the like.

Zeocin (zeomycin) is a member of the bleomycin antibiotic family. One could also use hygromycin, neomycin, blasticidin, puromycin, or mycophenolic acid resistance markers and antibiotics and the like as selection markers.

The present invention also provides methods of producing flavivirus reporter virus particles (RVPs). A reporter virus particle is a particle that comprises elements of a virus which are produced from a cell comprising a replicon and comprising any other elements necessary for the generation of the virus or virus-like particle. The RVP also comprises a reporter gene. The presence of the reporter gene can be used to monitor the particle's assembly, replication, infection ability, and the like.

In some embodiments, a method of producing flavivirus RVPs comprises contacting a cell with a nucleic acid sequence encoding a replicon. In some embodiments, the nucleic acid molecule encoding a replicon comprises a DNA molecule that encodes an RNA sequence. The RVPs are then produced once the cell has taken up the replicon. The nucleic acid sequence can be any sequence described herein.

The nucleic acid molecule encoding the replicon can be contacted with the cell in any manner that enables the nucleic acid molecule encoding the replicon to enter the cell or to be transfected into the cell. Examples of methods of contacting a nucleic acid molecule encoding the replicon with a cell includes, but are not limited to, calcium phosphate transfection, lipid-mediated transfection, PEI-mediated transfection, electroporation, infection with a virus coding for the replicon, and the like.

In some embodiments, the cell that is contacted with the nucleic acid encoding a replicon comprises elements that can express the structural elements of the flavivirus such that when the replicon is expressed in the cell in conjunction with the structural elements, a RVP is produced. In some embodiments, the structural elements are stably expressed in the cell. Examples of structural elements that can be present in the producer cell include, but are not limited to, Capsid (C), pre-membrane protein (prM), Envelope protein (E), or combinations thereof.

In some embodiments the structural proteins are under control of an inducible promoter such that the expression is regulated by the presence or absence of a compound or other type of molecule. Any inducible promoter can be used. Examples of inducible promoters include, but are not limited to, tetracycline (TREx, Invitrogen), Rheoswitch (NEB), Ecdyson (Invitrogen, Stratagene), Cumate (Qbiogene), glucocorticoid responsive promoter, and the like.

In some embodiments, a producer cell can be used that has the structural proteins stably transfected under the control of an inducible promoter. For example, a HEK-293 cell can stably express the structural proteins of a flavivirus (e.g. C, prM, and E) under the control of a tetracycline inducible promoter. An example of such a cell line, which can be referred to as "CME 293trx," would express the capsid, pre-membrane protein, and envelope protein of a flavivirus under the control of a tetracycline inducible promoter.

When contacting the cells with the replicon the confluence or density of the cells on the plate, well, or other type of container can be modified to increase or decrease transfection efficiency. In some embodiments, the cells are contacted with the replicon when they are at 40-70% or about 50% to about 60%, or 50 to 60% confluence. Additionally, for example for transfection methods using calcium phosphate, the confluence of the cells is about 70%, whereas for cells that are transfected with a lipid mediated agent (e.g. lipofectamine) or PEI mediated agent (e.g. JetPEI) the cells can be at a confluence of about 90%.

As used herein, the term "about" refers to an amount that is +10% of the amount being modified. For example "about 10" includes from 9 to 11.

In some embodiments, the cell that is contacted with the nucleic acid molecule encoding the replicon is also contacted with reporter virus particle media. The "reporter virus particle media" is media that facilitates or enhances the production of reporter virus particles by maintaining the pH of media in which RVP-producing cells are growing (e.g. in a tissue culture well, dish, or flask). In some embodiments, the pH of the media is maintained at about 7 to about 9, about 7.5 to about 8.5, about 8, about 7.8 to about 8.2, or 8.

The harvesting of the particles can be done at any time after the nucleic acid encoding the replicon is contacted with the cell that is able to produce the RVPs after being contacted with the replicon. In some embodiments, the RVPs are harvested every 24 hours or at times 72-148 hours post-transfection. In some embodiments the RVPs are harvested every 6 to 8 hours. The RVPs can be harvested by collecting the supernatant of the media that the cells are growing in. The RVPs are then isolated from the media. Any method of isolation can be used to isolate or purify the RVPs away from the media. Examples of isolation and purification include, but are not limited to, filtering the cell media supernatant. The particles can also be isolated or collected by centrifugation. In some embodiments, the collecting of the particles comprises isolating the produced particles.

As described herein, the present invention provides a cell or "producer cell" that expresses the structural proteins or a replicon of a flavivirus. The present invention also provides cells comprising the structural proteins of a flavivirus (C, prM, E). In some embodiments, the cell comprising the structural proteins of a flavivirus does not comprise the non-structural proteins of a flavivirus. As used herein, when a cell is referred to as "comprising" a protein it can refer to a cell that is stably transfected and, therefore, stably expresses the protein(s) referred to or it can refer to a cell that is only transiently expressing the proteins. In some embodiments, the cell comprises (e.g. expresses) structural proteins of a flavivirus that include, but are not limited to, C, prM, E, or combinations thereof.

In some embodiments, the cell comprises an inducible promoter controlling the expression of the structural proteins or the replicon. In some embodiments, the structural genes and/or the inducible promoter are stably integrated into the cell. In some embodiments, the cell comprising the structural proteins of a flavivirus does not comprise the 5' untranslated region of the flavivirus. In some embodiments, the 5' untranslated region of the flavivirus includes any RNA sequence prior to the first ATG of the flavivirus. In some embodiments, the cell is free of 5' UTR of the flavivirus upstream of the ATG start codon of the flavivirus polyprotein comprising the secondary structure that influences translation of the polyprotein and/or the replication of the viral RNA genome.

In some embodiments, the producer cell comprises nucleic acid sequence that are optimized for protein expression as described herein. In some embodiments, the producer cell comprises a nucleic acid sequence that is codon optimized for the capsid protein expression as described herein. In some embodiments, the producer cell comprises a nucleic acid sequence that is not codon optimized for the capsid protein expression as described herein. In some embodiments, the producer cell comprises a nucleic acid sequence that is codon optimized for the prM and/or E protein expression. In some embodiments, the producer cell comprises a nucleic acid sequence that is not codon optimized for the prM and/or E protein expression.

The structural proteins can be expressed from one or more nucleic acid molecules. In some embodiments, the structural proteins are expressed from a single nucleic acid molecule. In some embodiments, the structural proteins that are expressed from a single nucleic acid molecule are under the control of one or more promoters. In some embodiments, a different promoter can control the expression of each protein, or a first promoter can control the expression of one structural protein and a second promoter can control the expression of the other structural proteins. For example, C, prM, and E can all be controlled by one promoter, or a first promoter can control the expression of C, while a second promoter controls the expression of prM and E. Another example includes, a first promoter operably linked to a nucleic acid molecule encoding the C protein, a second promoter operably linked to a nucleic acid molecule encoding the prM protein, and a third promoter operably linked to a nucleic acid molecule encoding the E protein.

In some embodiments, the nucleic acid molecule encoding the structural proteins is a stable integration. As used herein, "stable integration" refers to any non-endogenous nucleic acid molecule that has been taken up by a cell and has been integrated into the cell genome. Cells comprising a stable integration naturally replicate their genome with the integrated nucleic acid and pass the nucleic acid to daughter cells.

In some embodiments, the nucleic acid molecule encoding the structural proteins is a plasmid. In some embodiments, a cell comprising one or more nucleic acid molecules encoding for the structural proteins is a HEK-293 cell or a cell derived from a HEK-293 cell. As used herein, "a cell derived from a HEK-293 cell" is one where the HEK-293 is the parental cell line and has been modified in such a manner by either recombinant or other techniques such that it is no longer a "wild-type" HEK-293 cell.

As discussed above, the structural proteins can be under the control of one or more inducible promoters and thus one can regulate the production of RVPs. In some embodiments, methods of producing flavivirus RVPs comprise contacting a cell with a nucleic acid encoding a flavivirus replicon wherein the nucleic acid further comprises nucleic acids encoding the structural proteins of a flavivirus virus and an inducible promoter which controls expression of said nucleic acids encoding the structural proteins of a flavivirus. Upon contacting the cell with the nucleic acid encoding the replicon the structural proteins are induced. The induction of the expression of the structural proteins along with the presence of the replicon and the expression of the Dengue proteins from the replicon will result in the cell producing Dengue RVPs.

RVPs or other particles produced using Dengue replicons can use, in some embodiments, nucleic acid sequences as described herein. The particles can be produced by transfecting a producer cell a composition comprising a nucleic acid sequence as described herein. In some embodiments, the particles comprise a RNA sequence that is encoded by a sequence described herein. "A RNA sequence encoded by a sequence" refers to the relationship between the RNA sequence and the sequence that encodes for the RNA sequence. For example, the RNA sequence is encoded by SEQ ID NOs: 1-27, that is the RNA is transcribed from another nucleic acid sequence, such as a DNA sequence.

The present invention also provides compositions comprising flavivirus reporter virus particles and a storage buffer. The storage buffer is any buffer that allows the flavivirus reporter virus particles to be stored (e.g. frozen or refrigerated) for a period of time and the flavivirus reporter virus particles maintain their ability to infect a flavivirus susceptible cell (e.g. a cell that can be infected by a flavivirus virus or RVP). In some embodiments, the storage buffer is maintained at a pH of about 7.5 to about 8.5. In some embodiments, the pH of the storage buffer is 8. In some embodiments the storage buffer is Hepes buffer. In some embodiments, the concentration of HEPES is more than 10 mM. In some embodiments, the concentration of Hepes is 25 mM and/or has a pH of 7.5 to 8.5 or 8. In some embodiments, the storage buffer comprises an additive. As used herein, an "additive" may be any molecule that, when added to a storage buffer comprising RVPs, prevents degradation of RVPs. Examples of additives include, but are not limited to, bovine serum albumin (BSA), fetal calf serum, sugars, or combinations thereof. In some embodiments, the additive must be above a certain concentration in a weight/volume ratio. For instance, in some embodiments, the additive comprises 1% to 10%, 2% to 8%, 3% to 7%, 4% to 6%, or 5% D-Lactose per 100 mL of storage buffer. In some embodiments, the storage buffer comprises a protein additive. In some embodiments, the protein additive must be above a certain concentration in a volume/volume ratio. For instance, in some embodiments, the storage buffer comprises a protein additive at concentrations of 5% to 50%, 15% to 25%, or 20% fetal calf serum. In some embodiments, the total protein additive concentration of the storage buffer is at least 8 µg per mL of storage buffer upon addition of said protein additive.

The present invention also provides methods of infecting a cell with a RVP comprising contacting a cell with a flavivirus reporter virus particle. In some embodiments, the cell expresses DC-SIGNR or DC-SIGN. In some embodiments, the cell that expresses DC-SIGNR or DC-SIGN is a Raji-DC-SIGNR, Raji-DC-SIGN, BHK-DC-SIGNR, or BHK-DC-SIGN cell. In some embodiments the cell is a C636 cell or a K562 cell. In some embodiments, the RVP is contacted with the cell in the presence of fetal calf serum in the media. In some embodiments, the media comprises about 0.1% to about 10%, about 0.3% to about 3.0%, or about 0.5%, or 0.5% fetal calf serum.

The present invention also provides a method of identifying a compound that can inhibit flavivirus infection. In some embodiments, the method comprises contacting a cell with a flavivirus RVP in the presence or absence of a test compound and determining if the flavivirus RVP can infect said cell in the presence and absence of said test compound. If the flavivirus RVP can infect the cell in the absence of the test compound, but not in the presence of the test compound that can inhibit flavivirus infection, the test compound is said to be a compound that inhibits Dengue infection. The test compound that can inhibit flavivirus infection can be any type of compound or molecule including, but not limited to, a small organic molecule, small peptides, fusions of organic molecules and peptides, and the like. In some embodiments, the compound that can inhibit flavivirus infection is not an antibody, which can also be referred to as a neutralizing antibody. Infection can be measured or determined by any manner, but can be for example determined by measuring the expression of the reporter element in the cell. For example, if a flavivirus RVP comprises a GFP reporter, the ability to infect a cell can be determined by detecting the expression of GFP in the cell after being contacted with the RVP in the presence or absence of the test compound. If the test compound that can inhibit flavivirus infection is a compound that can inhibit the ability of the RVP to infect the cell, the GFP expression will be less than the GFP expression in the absence of the test compound.

The present invention also provides methods of identifying a compound that inhibits flavivirus assembly comprising contacting a flavivirus RVP producer cell with a test compound and determining if the flavivirus RVPs can assemble in the presence of said test compound. A compound that inhibits flavivirus assembly can be any compound including but not necessarily limited to small organic compounds, peptides, complete antibodies, any portion of antibody, or fusion compounds of any combination thereof. If assembly is prevented in the presence of the test compound as compared to the assembly in the absence of the test compound, the test compound is said to be a compound that inhibits flavivirus assembly. A flavivirus RVP producer cell is a cell that is capable of producing flavivirus RVPs. Producer cells can be generated in any manner including the methods described herein. For example, the method can comprise transfecting the producer with a nucleic acid molecule encoding a flavivirus replicon. Assembly can be measured by any manner including measuring the expression of the reporter construct that is part of the RVP, such as, but not limited to, GFP expression. Assembly can also be measured by detecting reporter virus and/or subviral particles in the media by detection of E protein, for example using an ELISA or western blot.

The present invention also provides methods of identifying a compound that inhibits flavivirus RNA replication comprising contacting a cell comprising a flavivirus replicon with a test compound and measuring flavivirus RNA replication, wherein a decrease in flavivirus RNA replication indicates that said test compound is a compound that inhibits flavivirus RNA replication. A compound that inhibits flavivirus RNA replication can be any compound including but not necessarily limited to small organic compounds, peptides, complete antibodies, any portion of antibody, or fusion compounds of any combination thereof. RNA replication can be measured by any method, but can also be determined by measuring the RNA replication or expression of the reporter element by the replicon. For example, if the replicon comprises a GFP reporter, the GFP expression in the cell can be measured to determine if the test compound inhibits RNA replication.

The present invention also provides methods of identifying neutralizing antibodies against a flavivirus. In some embodiments, the method comprises contacting a flavivirus RVP with a test antibody; contacting the mixture of the RVP and the test antibody with a cell that can be infected with the RVP in the absence of the test antibody; and measuring the infection of said cell in the presence of said test antibody. If the ability of the RVP to infect the cell is decreased in the presence of the test antibody as compared to when the antibody is not present, this indicates that the test antibody is a neutralizing antibody against the flavivirus. As discussed above, RVP infection can be determined by any method, including, but not limited to measuring reporter expression after infection in the cells. In some embodiments, the reporter is GFP. The test antibody can be any type of antibody including monoclonal antibodies, polyclonal antibodies, antibody fragments, single chain antibodies, scFV, and the like. The antibodies can also be humanized antibodies. The antibodies can also be antibodies from an individual's sera or isolated from an individual.

In some embodiments, the test antibody is a serotype-specific flavivirus antibody and the flavivirus RVP is a serotype-specific flavivirus reporter virus particle. For example, Dengue virus has four serotypes (Dengue 1, Dengue 2, Dengue 3, and Dengue 4). The serotypes can be any of the four serotypes of Dengue virus or any future serotypes of Dengue that are identified. The present invention can also be used to identify serotype-specific neutralizing antibodies by monitoring the association between a test antibody against a serotype-specific flavivirus RVP. If a test antibody is a neutralizing antibody against one serotype, but not another, it is said to be specific to at least one serotype of a flavivirus. A neutralizing antibody can also be neutralizing for more than one serotype but not for all serotypes and such neutralizing antibodies can be identified using the methods described herein.

In some embodiments, RVPs are produced by introducing a nucleic acid sequence encoding C, prM, and E into a cell that comprises a replicon. In some embodiments, the cell is stably expressing the replicon. In some embodiments, the cell is transiently expressing the replicon. In some embodiments, nucleic acid sequences encoding the replicon and C, prM and E are introduced simultaneously into the cell. Techniques to introduce a nucleic acid molecule into a cell are described herein and known to one of skill in the art. Any method of introducing a nucleic acid molecule into a cell can be used. In some embodiments, the method of introducing a nucleic acid molecule into a cell is transfection. Transfection includes the introduction of isolated nucleic acid into a cell, for example not limited to, by precipitation, endocytosis, lipid fusion, or electroporation. Transfection does not include the introduction of nucleic acid into a cell by a virus. Virus transduction includes the introduction of a specific nucleic acid into a cell by a virus. In some embodiments, the nucleic acid molecule is transferred to the cell in the absence of a virus or without using the method of virus transduction.

The present invention also provides isolated nucleic acid molecules comprising a nucleic acid sequence encoding a flavivirus capsid polypeptide and a nucleic acid sequence encoding a flavivirus prME polypeptide. In some embodiments, the nucleic acid sequence encoding the capsid polypeptide is not codon optimized for protein expression. In some embodiments, the nucleic acid sequence encoding the capsid polypeptide is codon optimized for protein expression. In some embodiments, the nucleic acid sequence encoding the prME polypeptide is codon optimized for protein expression. In some embodiments, the nucleic acid molecule comprises a nucleic acid sequence encoding a capsid polypeptide that is not codon optimized and a nucleic acid sequence encoding a prME polypeptide that is codon optimized. In some embodiments, the nucleic acid sequence encoding a prME polypeptide is not codon optimized.

The nucleic acid sequences described herein encoding the capsid polypeptide and/or the prME polypeptide can be combined into a single sequence or kept as distinct separate nucleic acid molecules as described herein. The nucleic acid sequences can also be operably linked to one or more promoters as described herein. In some embodiments, a first nucleic acid molecule comprises a nucleic acid sequence encoding the capsid polypeptide and the prM polypeptide and a second nucleic acid molecule comprises a sequence encoding the Envelope polypeptide. In some embodiments, a first nucleic acid molecule comprises a sequence encoding the capsid polypeptide and a second nucleic acid molecule comprises a sequence encoding the prME polypeptide.

As used herein "codon optimized," refers to a nucleic acid sequence that has been modified where the one or more modification results in increased protein expression as compared to the unmodified nucleic acid sequence. Codon optimization also refers to where a nucleic acid sequence is modified that results in enhanced expression in a eukaryotic cell by replacing one or more codons of the native sequence with codons that are more frequently or most frequently used in the genes of the eukaryotic cell. Various species exhibit particular bias for certain codons of a particular amino acid. In some embodiments, the increase in expression (e.g. protein expression) is at least 10%, 20%, 30%, 40%, 50%, 60%, 70%, 80%, 90% more than the non-optimized sequence. In some embodiments, the increase in expression is at least 100%, 200%, 300%, 400% or 500% more than the non-optimized sequence. The comparison can be made using any technique. The unmodified nucleic acid sequence can also be referred to as the wild-type sequence or a sequence that is found in nature.

Most amino acids are encoded by multiple synonymous codons. Different organisms use synonymous codons with different frequencies, a phenomenon known as codon bias. Preferred codon usage has been identified as an important factor in the efficiency of both prokaryotic and eukaryotic gene expression (Gustafsson et al., Trends in Biotechnology 22(7), 2004). The presence of infrequently used codons in messenger RNAs can result in decreased expression of exogenous genes. This is especially true for the expression of viral genes, which are often A-T rich and encode cis-acting negative regulatory sequences (Gustafsson et al., Trends in Biotechnology 22(7), 2004).

Codon optimization is a methodology used to improve heterologous protein expression by altering the codon usage of target genes. Codon optimization introduces silent nucleotide changes to remove rare codons and replace them with more commonly used codons that reflect the codon bias of a given host cell. Additionally, codon optimization employs computer algorithms to analyze gene sequences for silent nucleotide changes that can improve a variety of important factors involved in different stages of protein expression including mRNA secondary structure, mRNA nuclear export, and translational cis-elements. Codon optimization of several viral genes, including the E5 gene of human papillomavirus (HPV) and the U51 gene from human herpesvirus (HHV), results in enhanced protein expression in mammalian cells (Disbrow et al., Virology 311, 2003; Bradel-Tretheway et al., Journal of Virological Methods 111, 2003). In some embodiments, coding sequences for Dengue structural proteins are codon optimized and used for expression in eukaryotic (e.g. mammalian) cells. An example of the cell used can be, but is not limited to, HEK-293T cells.

Viral proteins and proteins that are naturally expressed at low levels can provide challenges for efficient expression by recombinant means. In addition, viral proteins often display a codon usage that is inefficiently translated in a host cell (e.g., a mammalian cell). Alteration of the codons native to the viral sequence can facilitate more robust expression of these proteins. Codon preferences for abundantly expressed proteins have been determined in a number of species, and can provide guidelines for codon substitution. Synthesis of codon-optimized sequences can be achieved by substitution of viral codons in cloned sequences, e.g., by site-directed mutagenesis, or by construction of oligonucleotides corresponding to the optimized sequence by chemical synthesis. See, e.g., Mirzabekov et al., J. Biol. Chem., 274(40):28745-50, 1999. The optimization can also include consideration of other factors such as the efficiency with which the sequence can be synthesized in vitro (e.g., as oligonucleotide segments) and the presence of other features that affect expression of the nucleic acid in a cell. For example, sequences that result in RNAs predicted to have a high degree of secondary structure are normally avoided. AT- and GC-rich sequences that interfere with DNA synthesis also routinely avoided. Other motifs that can be detrimental to expression include internal TATA boxes, chi-sites, ribosomal entry sites, cryptic splice donor and acceptor sites, and branch points. These features can be identified manually or by computer software and they can be excluded from the optimized sequences.

In some embodiments, the capsid polypeptide that is encoded by the nucleic acid sequence is from the same flavivirus as the prME polypeptide. In some embodiments, the capsid polypeptide encoded by the nucleic acid sequence and the prME polypeptide encoded by the nucleic acid sequence are from the same flavivirus but from different serotypes. For example, the Capsid may be from DENV1 and the prME may be from DENV2. In some embodiments, the capsid is DENV1, DENV2, DENV3, or DENV4, and the prME is independently DENV1, DENV2, DENV3, or DENV4. In some embodiments, the prM and E are also from different serotypes or different flaviviruses. Therefore, in some embodiments, the nucleic acid sequence encoding the capsid polypeptide, the nucleic acid sequence prM polypeptide and the nucleic acid sequence encoding the Envelope polypeptide can be from the same flavivirus and the same serotype or they can each be independently from different flaviviruses and different serotypes. The resulting chimeric nucleic acid sequences could encode for three proteins that are from same virus, same serotype, different viruses, and/or different serotypes of the same virus.

The present invention also provides host cells and isolated cells comprising any nucleic acid molecule described herein and a replicon. In some embodiment, the nucleic acid molecule encoding the replicon and the nucleic acid molecule encoding the capsid are from the same flavivirus, from different flaviviruses, from the same flavivirus and the same serotype, or from the same flavivirus and different serotypes. For example, the replicon may be from DENV1 and the capsid may be from DENV2. In some embodiments, the replicon may be from DENV2, the capsid may be from DENV2, and the prME may be from DENV4.

The replicons described throughout the present application can be any flavivirus replicon including but not limited to the Dengue replicon. Examples of Dengue replicons include, but are not limited to, DENV1 replicon, DENV2 replicon, DENV3 replicon, and DENV4 replicon.

The CprME polypeptide can be expressed as a single polypeptide. When expressed as a single polypeptide the polypeptide is cleaved to generate the capsid protein and the Envelope protein. There can be a cleavage sequence between the sequences of the Capsid polypeptide and the prME polypeptide. There is also a cleavage sequence that cleaves in the prME polypeptide that generates the envelope polypeptide. In some embodiments, any cleavage site that is encoded by a nucleic acid sequence can be a nucleic acid sequence that is from a different or the same serotype as the replicon or the capsid polypeptide. The cleavage site can also be from the same or a different flavivirus. In some embodiments, the cleavage sequence is a sequence comprising SEQ ID NO: 24, 25, 26, or 27. In some embodiments a nucleic acid sequence encodes the cleavage sequence. In some embodiments, the nucleic acid sequence encoding the cleavage sequence encodes an amino sequence comprising SEQ ID NO: 24, 25, 26, or 27.

The cells described herein can also in some embodiment comprise a flavivirus NS3 protein. In some embodiments, the nucleic acid molecule that encodes a cleavage site is a sequence that is from the same or different serotype as the NS3 protein. The nucleic acid sequence can also be from the same or different flavivirus.

Other combinations include where the replicon and the capsid are from the same or different serotypes or are from the same or different flaviviruses.

In some embodiments, the present invention provides flavivirus particles comprising the nucleic acid molecules described herein. In some embodiments, the particles comprise the reporters as they are described herein. In some embodiments, the particles comprise polypeptides encoded by nucleic acid molecules described herein.

In some embodiments, the nucleic acid molecule comprises a sequence of SEQ ID NO:1, SEQ ID NO: 2, SEQ ID NO: 3, SEQ ID NO: 4, SEQ ID NO: 6, SEQ ID NO: 8, or SEQ ID NO: 22. In some embodiments, the nucleic acid molecule comprises a sequence encoding an amino acid sequence comprising SEQ ID NOs: 5, 7, 9, or 23. The sequences can also be optimized to increase protein expression in a host cell, such as but not limited to a eukaryotic cell. Examples of cells that can be used include, but are not limited to mammalian, avian, insect, bacterial, and the like. Examples of host cells include, but are not limited to, human cells, rodent (e.g. mouse or rat), insect (e.g. mosquito), horse, cat, dog, pig, and the like. In some embodiments, the optimized sequence is SEQ ID NO: 1 or 3. In some embodiments the chimeric sequence is SEQ ID NO: 2 or 4 or an optimized version thereof.

In some embodiments, the present invention provides a nucleic acid comprising a plasmid DNA molecule encoding a replicon of DEN, wherein said nucleic acid molecule is free of nucleic acid sequences encoding at least one full-length structural protein of DEN, wherein said replicon is under the control of a promoter constitutively active in mammalian cells, wherein said replicon encodes a fluorescent or luminescent reporter. The term "full-length structural protein" of a flavivirus or a Dengue refers to any structural protein of the flavivirus. In some embodiments, the structural protein is Capsid (C), premembrane protein (prM) and envelope glycoprotein (E). Thus, in some embodiments, the nucleic acid sequence is free of at least a sequence that encodes a full length Capsid (C), premembrane protein (prM), envelope glycoprotein (E), or combination thereof. In some embodiments, the full length sequence is the sequences described herein.

The present application described various sequences. In some embodiments, a nucleic acid sequence or an amino acid sequence is at least 80, 85, 90, 95%, 96%, 97%, 98%, or 99% similar to a sequence described herein. For example, in some embodiments, an optimized sequence is at least 80, 85, 90, 95%, 96%, 97%, 98%, or 99% similar to SEQ ID NOs: 1-27. In some embodiments, a sequence comprises at least 100, 200, 300, 400, 500, 600, 700, 800, 900, 1000, 1100, 1200, 1300, 1400, 1500, 1600, 1700, 1800, 1900, or 2000 nucleotides or amino acid residues of a sequence described herein, such as but not limited to SEQ ID NOs: 1-27.

Similarity can be determined by using the default settings BLAST (basic local alignment search tool) to align two sequences. For example, for sequence comparison, typically one sequence acts as a reference sequence, to which a second (test) sequence may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman (Adv. Appl. Math. 2: 484 (1981)), by the algorithm of Needleman & Wunsch (J. Mol. Biol. 48: 443 (1970) (by the search for similarity method of Pearson & Lipman (Proc. Nat'l. Acad. Sci. USA 85:2444 (1988)), by computer implementations of these algorithms (GAP, BESTFIT, FASTA, and TFASTA-Sequence Analysis Software Package of the Genetics Computer Group, University of Wisconsin Biotechnology Center, 1710 University Avenue, Madison, Wis. 53705), or by visual inspection (see Current Protocols in Molecular Biology, F. M. Ausbel et al, eds, Current Protocols, a joint venture between Greene Publishing Associates, In. And John Wiley & Sons, Inc. (1995

Supplement) Ausbubel). Examples of algorithms suitable for determining percent sequence similarity are the BLAST and BLAST 2.0 algorithms (see Altschul (1990) J. Mol. Biol. 215: pp. 403-410; and www.ncbi.nlm.nih.gov of the National Center for Biotechnology Information).

Therefore, in some embodiments, the nucleic acid molecule is free of nucleic acid sequences encoding at least one structural protein of the flavivirus, such as the Dengue virus. The nucleic acid sequence may encode for a structural protein, but in some embodiments, the nucleic acid molecule cannot encode all of the full length structural proteins of the virus. In some embodiments, the nucleic acid molecule does not encode a full length Capsid (C), premembrane protein (prM) or envelope glycoprotein (E). The structural proteins can be from any flavivirus as described herein, including but not limited to Dengue.

In some embodiments, the present invention provides a method of infecting target cells with dengue reporter virus particles (RVPs). In some embodiments, the method comprises transfecting a producer cell with a plasmid DNA molecule encoding a replicon of DENV or a nucleic acid molecule as described herein. In some embodiments, the method comprises collecting a RVP in the supernatant from the transfected producer cell, and infecting permissive target cells with the RVPs. In some embodiments, the producer cell takes up the plasmid DNA molecule, expresses the replicon of DEN, and produces DENV RVPs that are released from the producer cell. In some embodiments, the producer cell expresses the C, prM, E proteins, or any combination thereof of DENV from an inducible promoter, wherein said capsid (C) is not codon optimized for protein expression and said prM and E proteins are codon optimized for protein expression. In some embodiments, the replicon is under the control of a promoter constitutively active in mammalian cells. In some embodiments, the transfection is done without RNA or is free of RNA. In some embodiments, the replicon is free of nucleic acid sequences encoding at least one full-length structural protein of DENV. In some embodiments, the replicon comprises a nucleic acid sequence encoding a reporter. In some embodiments, the reporter is expressed upon RVP infection of the target cell.

As used herein, the phrase "transfection is done without RNA or is free of RNA" refers to the step of transfecting a producer cell with a plasmid DNA molecule. Therefore, in some embodiments, the step of transfecting a producer cell is done in the absence of RNA or is free of RNA in the transfection mixture that is transfected or contacted with the producer cell.

The transfection step of any method described herein can be done using any technique including, but not limited to calcium phosphate mediated transfection, lipid mediated transfections, PEI (Polyethylenimine) mediated transfection and the like. Lipid mediated transfection refers to lipid based transfection reagents, such as but not limited to lipofectamine. Any transfection method can be used and is not limited by the examples described herein.

In some embodiments, the present invention provides methods of infecting target cells with dengue reporter virus particles (RVPs) by transfecting a producer cell with a plasmid DNA molecule encoding C, prM, and E proteins of a flavivirus (e.g. DEN). In some embodiments, the method comprises collecting RVPs in the supernatant from the transfected producer cell, and infecting permissive target cells with said RVPs. In some embodiments, the producer cell expresses a replicon (e.g. a dengue replicon). In some embodiments, the replicon is free of nucleic acid sequences encoding at least one full-length structural protein of a flavivirus (e.g. DEN). In some embodiments, the producer cell takes up the plasmid DNA molecule, expresses the C, prM, and E proteins of the flavivirus (e.g. DEN), and produces DENV RVPs that are released from the producer cell. In some embodiments, the capsid protein is not codon optimized for protein expression and the prM and E proteins are codon optimized for protein expression.

In some embodiments of the present invention, the capsid protein is the same serotype as the replicon.

Methods involving transfection are described herein. In some embodiments of a method of transfecting a cell, the transfection step is free of RNA.

In some embodiments, the replicons described herein comprise a nucleic acid molecule encoding a reporter. Reporter can be any enzyme or protein that can be used as a reporter or a read out. For example, the reporter can be a fluorescent protein or luciferase enzyme, and the like. In some embodiments, the reporter is expressed from the cell once the RVP infects the target cell.

In some embodiments, the present invention provides methods of identifying a compound that inhibits flavivirus (e.g. dengue) assembly comprising contacting a flavivirus (e.g. dengue) RVP producer cell with a test compound and determining if the flavivirus (e.g. dengue) RVPs can assemble in the presence of the test compound, wherein if assembly is prevented the test compound is said to be a compound that inhibits DENV assembly.

In some embodiments, the present invention provides methods of identifying a compound that inhibits flavivirus (e.g. dengue) RNA replication comprising contacting a cell containing a flavivirus (e.g. dengue) replicon with a test compound and measuring replicon replication, wherein a decrease in replicon replication indicates that the test compound is a compound that inhibits DENV RNA replication.

In some embodiments, the present invention provides methods of generating antibodies against a flavivirus comprising contacting a flavivirus particle that is described herein or generated by a method described herein with a mammal and generating said antibody. Methods of making antibodies are well known and any such method can be used provided that the particles that are described herein are used as the antigen to generate the antibody. In some embodiments, the antibody is isolated. The antibody can be a polyclonal or monoclonal. In some embodiments, the antibody is a human antibody, a humanized antibody, a chimeric antibody, and the like. In some embodiments, the antibody is antigen specific, which means that the antibody does not significantly cross-react with another antigen and only binds to the antigen that the antibody was raised against.

Antibodies are well known in the art and methods of making antibodies are routine. For example, intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Non-limiting examples of binding fragments encompassed within the term "antigen-specific antibody" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)$_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof.

The antibodies to the particles or the antigens described herein can be obtained using conventional techniques known to those skilled in the art, and the fragments are screened for binding in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and Biacore analysis, to identify one or more hybridomas that produce an antibody that specifically interacts with a molecule or compound of interest.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature.

The term "capture reagent" can also refer to chimeric antibodies, such as humanized antibodies, as well as fully humanized antibodies.

In some embodiments, the present invention provides methods of generating an immune response in a mammal against a flavivirus particle comprising contacting a mammal with the particle under conditions sufficient to generate an immune response. In some embodiments, the immune response is a response that generates antibodies against the particle. The immune response can be against the surface proteins of the particle.

The antibodies and/or the immune response can be generated in a mammal, such as but not limited to, a human, mouse, rat, sheep, dog, pig, cat, monkey, horse, and the like.

The invention is now described with reference to the following examples. These examples are provided for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLE 1

Construction of a codon-optimized chimeric DENV CprME sequence. The structural genes for Dengue viruses encode for Capsid (C) Premembrane (prM) and Envelope (E) proteins (FIG. 1A). CprME sequence for Dengue serotype 2 was PCR amplified using clone 516803 with the following primers 5'-caccATGAATAACCAACGGAAAAAGGCGA-3' (SEQ ID NO: 10) and 5'-TTTCACTATTAGGCCTGCAC-CATGACTCCCAAATAC-3' (SEQ ID NO: 11). This PCR product was cloned into pENTR/D topo and subsequently moved into the expression vector pTRex-DEST-30, containing a CMV promoter and tetracycline operator sites. CprME sequence of Dengue serotype 4 was obtained by RT-PCR from RNA isolated from TVP360 virions using the following primers 5'-GGTTGATGGGCGGCCGCCACCATGAAC-CAACGAAAAAAGGTGGTTAGAC-3' (SEQ ID NO: 12) and 5'-CCCTCTAGAGCGGCCTTATGCTTGAACT-GTGAAGCCCAGAAACA-3' (SEQ ID NO: 13) and was Infusion cloned as a NotI fragment into the TRex-pBR322 plasmid described below.

Plasmids containing wt DENV3 sequence are reported to be highly unstable in *E. coli* (Chen et al. Journal of Virology: 69(8)). To generate a DENV3 plasmid capable of CprME expression, a codon optimized DENV3 sequence for CprME (DENV3opt) that is biased towards human codon usage was synthesized. Codon optimization is often useful for increasing the expression of viral proteins in human cells. The DENV3opt sequence was cloned as a NotI-MluI fragment into a modified version of the TRex-DEST-30 plasmid, which is called TRex-pBR322, which still contains a CMV promoter and tetracycline operator sites and also contains the ROP protein which results in a lower copy plasmid that is more suitable for cloning of unstable viral inserts such as DENV3 CprME. The codon optimized DENV3 sequence was found to be stable in this plasmid. Additionally, high levels of expression of DENV3opt CprME viral proteins in HEK-293T cells from this plasmid were observed. Surprisingly, however, high levels of expression of CprME proteins from DENV3opt plasmids did not support correspondingly high levels of RVP production. Additionally, expression of DENV4 wt, although having a very similar Capsid amino acid sequence to DENV2, did not result in high levels of RVP production. This may be due to inefficient packaging of the DENV2 replicon by the DENV3opt Capsid or the DENV4 wt Capsid. Alternatively, the loss of secondary structure in the DENV3opt Capsid may result in inappropriate translational start site utilization.

In an effort to optimize RVP production using the DENV3opt, DENV4 wt, and DENV4opt sequences, several chimeric constructs encoding Capsid protein from serotype 2 (the same serotype as the replicon) and prME from either serotype 3 or 4 were made. DENV2 Capsid by PCR Infusion into the XbaI and MluI sites of TRex-pBR322 was cloned with the following oligonucleotides (5'-GCCTCCG-GACTCTAGcggccgccaccATGAATAAC-CAACGGAAAAAGGCGA-3' (SEQ ID NO: 14) and 5'-CGTCGCATGCACGCGtcatgccgcg-gaTCTGCGTCTCCTATTCAAGATGTTCAGCAT-3') (SEQ ID NO: 15). Subsequently, prME sequence from codon optimized DENV3 was PCR amplified with the following oligonucleotides 5'-AGGAGACGCAGATCCAGCTTAT-GTCTGATGATGATGCTGCCTGCCA-3' (SEQ ID NO: 16) and 5'-TGCACGCGTCATGCCCTAAGCGGCCTG-CACCACGGCGCCGAG-3' (SEQ ID NO: 17) and In-Fusion cloned into the SacII site of TRex-pBR322 in frame with the DENV2 Capsid sequence.

To generate the DENV2/4 chimeric plasmid, wt prME sequence from DENV4 was PCR amplified using the following primers 5'-AGGAGACGCAGATCCACGATAACAT-TGCTGTGCTTGATTCCCA-3' (SEQ ID NO: 18) and 5'-TGCACGCGTCATGCCTCAGGCCTGCACG-GTGAAGCCCAGAAACA-3' (SEQ ID NO: 19) and Infusion cloned into TRex-pBR322 in frame with the DENV2 Capsid sequence using the SacII site.

Similarly, to generate the DENV2/4opt chimeric plasmid, codon optimized prME sequence of DENV4 was PCR amplified using the following oligonucleotides 5'-AGGAGACG-CAGATCCACCATCACACTGCTGTGCCTGATTCCCA-3' (SEQ ID NO: 20) and 5'-TGCACGCGTCATGCCTCAGGCCTGCACG-GTGAAGCCCAGAAACA-3' (SEQ ID NO: 21) and Infusion cloned into TRex-pBR322 in frame with the DENV2 Capsid sequence using the SacII site.

Cleavage of the Dengue polyprotein by the NS3 protease occurs between the Capsid and prM proteins (FIG. 1B). The NS3 cleavage site is highly conserved between different Dengue serotypes. Cleavage occurs between a conserved Argenine-Serine pair in all Dengue serotypes except for serotype 3, where it occurs between a Lysine-Threonine pair. For the DENV2/3opt chimera, sequences used encoded the conserved Argenine-Serine pair present in DENV2 for the C-prM cleavage site in order to optimize cleavage by the NS3 protease encoded by the DENV2 replicon. The chimeric cleavage sites are comprised of an RRRRS sequence, which are optimal for cleavage by the NS3 proteases of all 4 serotypes (Li et al. 2005).

EXAMPLE 2

Expression of DENV3 structural proteins from a codon-optimized DENV CprME sequence. DENV plasmids were used to test for expression of Dengue structural proteins in HEK-293T cells. Cells were plated in 384-well format at a density of 24,000 cells/well and transfected with plasmids encoding the CprME proteins from DENV1 wt, DENV2 wt, DENV3opt, and DENV4 wt using Lipofectamine 2000. 24 hours post transfection, cells were fixed in methanol and processed for immunofluorescence using a monoclonal antibody, 4G2 (100 µg/ml), which recognizes structural proteins of all 4 Dengue serotypes. Secondary antibody detection was with an anti-mouse Cy2 antibody. 293T cells transfected with wildtype DENV1, DENV2, and DENV4 constructs all exhibited faint staining with the 4G2 antibody. In contrast, cells transfected with the codon optimized DENV3 plasmid exhibited bright 4G2 staining, indicating that codon optimization of DENV3 results in enhanced expression of CprME in HEK-293T cells (FIG. 2).

EXAMPLE 3

Codon optimization of DENV2 CprME results in enhanced expression of Dengue structural proteins. Plasmids encoding wt DENV2 and codon optimized DENV2 are transfected into HEK-293T cells, or other eukaryotic cell types that can be transfected and that can express DENV proteins, to compare the expression levels of CprME. Cells are plated in 384-well format at a density of 24,000 cells/well and transfected with DENV2 wt or DENV2opt using Lipofectamine 2000. 24 hours post transfection, cells are fixed in methanol and processed for immunofluorescence using the monoclonal antibody 4G2 (100 µg/ml) with an anti-mouse Cy2 secondary antibody. HEK-293T cells transfected with DENV2 wt exhibit faint staining with the 4G2 antibody. In contrast, cells transfected with the codon optimized DENV2 plasmid exhibit bright 4G2 staining and express higher levels of CprME proteins.

EXAMPLE 4

Figure 3:
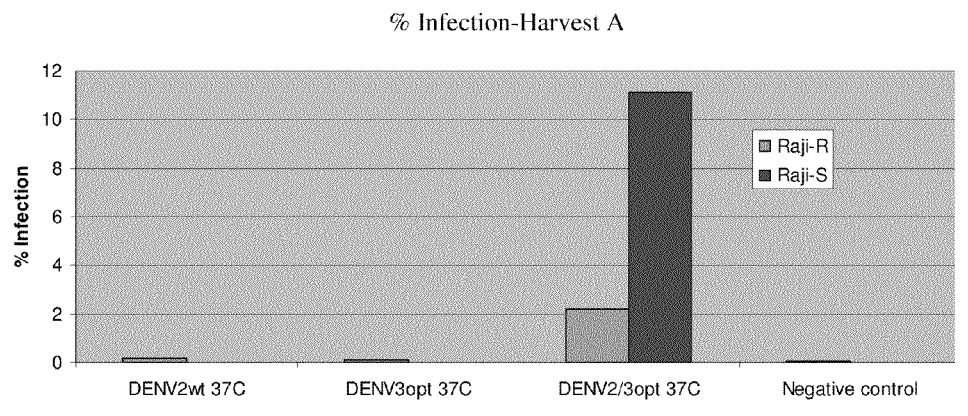

Production of DENV3 RVPs using a codon optimized DENV2/3opt chimera. The ability of the DENV3opt sequence to support RVP production in BHK-21 clone 15 cells was examined. The wild type DENV2, codon optimized DENV3opt, and the chimeric DENV2/3opt plasmids were used in this experiment. To produce Dengue reporter virus particles (RVPs) expressing GFP, BHK21-clone 15 cells, which carry a DENV2 GFP replicon stably maintained under zeocin selection, were transfected using Lipofectamine 2000 at 75-80% confluency with each of the above plasmids. 4-8 hours post transfection, the media was replaced with RVP production media (DMEM-10% FCS, 1% penicillin/streptomycin solution, 2 mM L-alanyl L-glutamine solution, 25 mM HEPES, pH 8.0) and cells were cultured at 37° C. with 5% CO2. The supernatants containing RVPs were collected at 48 hours post transfection (Harvest A). Supernatants were filtered through 0.45 µm syringe filters, aliquoted, and frozen in a dry-ice ethanol bath for 15 minutes. RVPs were subsequently stored at −80° C. For infection experiments, RVPs were thawed in a 37° C. water bath and used to infect suspensions of Raji DC-SIGN-R or Raji DC-SIGN cell lines permissive for Dengue infection. Raji DC-SIGN-R or Raji DC-SIGN were both infected because different Dengue serotypes display preferential infection of these two cell lines. For infection, 96 well plates were seeded at a density of 40,000 cells in 100 µl of RPMI media. Equal volumes of serially diluted RVPs were added to each well and cells were incubated at 37° C. 72 hours post infection, cells were fixed in 2% paraformaldehyde. Infected cells were quantified for GFP fluorescence by flow cytometry. As a negative control, BHK21-clone 15 cells were mock transfected and their supernatants used for infection of Raji-DC-SIGN-R or Raji DC-SIGN cell lines (FIG. 3). Under these conditions, expression of DENV2 wt and DENV3opt did not produce significant amounts of infectious RVPs, while expression of the DENV2/3 optimized chimera did. These experiments demonstrate that although codon optimized DENV3opt expresses CprME proteins at high levels, it does not result in productive RVPs, emphasizing that RVP production does not always correlate with DENV structural protein expression. Importantly, these experiments demonstrate that the failure of DENV3opt sequences to produce RVPs can be rescued by making a chimera of wild type DENV2 Capsid protein with DENV3opt prME proteins. This is likely due to an enhanced interaction between Capsid proteins and replicons of the same serotype. Alternatively, the sequence encoding the DENV2 Capsid may restore proper RNA secondary structure and start site utilization for the Capsid protein otherwise disrupted by codon optimization of the DENV3 Capsid.

EXAMPLE 5

Production of DENV4 RVPs using both a codon optimized and non codon optimized DENV2/4 chimera. RVPs for DENV4 wt, and chimeras DENV2/4 wt, DENV2/4opt and DENV2/3opt were produced by Lipofectamine transfection of Dengue specific plasmids (stated above) into BHK21-clone 15 cells, which maintain the DENV2 Luciferase replicon under Zeocin selection. Cells were transfected using Lipofectamine 2000 at 75-80% confluency with each of the above plasmids, and at 4-8 hours post transfection the media was replaced with RVP production media and cells cultured at 37° C. and 5% CO2. The supernatants containing RVPs were collected at 48 hours (Harvest A) and 72 hours (Harvest B) post transfection. Harvested supernatants were passed through 0.45 μm syringe filters, aliquoted and frozen in a dry-ice ethanol bath for 15 minutes. RVPs were stored at −80° C. until needed. For infection experiments, RVPs were thawed in a 37° C. water bath and used to infect BHK-DC SIGN cells in quadruplicate. 72 hours post infection, BHK-DC SIGN cells were lysed and prepared using the *Renilla* Luciferase Assay System as recommended by the manufacturer. Luminescence readings were measured using a Wallac luminometer, and the relative units are shown in FIG. 4. As a positive control for infectivity, cells were infected with previously validated RVPs that had been produced by transfection of the DENV luciferase replicon into 293 TRex cells conditionally expressing DENV2 wt CprME. These experiments demonstrate that RVPs produced using the DENV2/4 wt chimera yield more infectious particles than those produced using the DENV4 wt CprME construct. However, codon optimization of DENV4 prME sequence in the context of the DENV2 chimera does not further enhance infectivity in this production system, even though DENV2/4opt prME expresses better in cells. Overall, the greatest infectivity was displayed by RVPs produced from the codon optimized DENV2/3opt chimera, used as a positive transfection control for this experiment. Similar results were obtained with RVPs harvested 72 hours post transfection (Harvest B).

EXAMPLE 6

Inducible expression of Dengue structural proteins CprME using TRex stable cell lines. Using TRex 293 cells, stable cell lines that conditionally express Dengue serotype specific CprME proteins under tetracycline regulation were generated. To do this, 293 TRex cells were plated in 6 well dishes at a density of one million cells per well in complete medium (DMEM-10% FCS, 1% penicillin/streptomycin solution, 2 mM L-alanyl L-glutamine solution, 25 mM HEPES, pH 8.0). Plasmids encoding DENV4 wt, chimera DENV2/4 wt, and codon optimized chimera DENV2/4opt were transfected into 293 TRex cells using Lipofectamine 2000 as recommended by the manufacturer. Cells were trypsinized 48 hours post transfection and plated in T-75 flasks with complete medium, supplemented with 500 μg/ml of G418 and 10 μg/ml of blasticidin. Transfected cells were cultured for three weeks in selective media with trypsinization and reseeding upon reaching near confluence. Selected cells were then pooled, aliquoted, and subsequently frozen in fetal bovine serum supplemented with 10% DMSO. Cells were kept in liquid nitrogen for long term storage. To test for expression of CprME proteins, these cell lines were thawed, split into 6 well dishes, and cultured at 37° C. in the presence or absence of 100 ng/ml of doxycycline for 36 hours. Cells were then fixed using methanol and stained with the monoclonal antibody 4G2 (100 μg/ml) in conjunction with a Cy-3 anti-mouse secondary antibody at the recommended dilution in antibody block solution (PBS+Mg+Ca, 10% normal goat serum). Cells were examined for Dengue structural protein expression by immunofluorescence microscopy. CprME protein expression was observed only in the presence of doxycycline in the culture medium, thus validating the CprME 293 TRex conditional cell lines. No expression difference was observed between the DENV4 wt plasmid and the chimeric DENV2/4 wt plasmid. Thus, chimeric DENV sequences do not always show enhanced expression compared to the wild type versions. However, the codon-optimized chimera DENV2/4opt exhibited a much higher level of expression, indicating that codon optimization for DENV4 prME sequences enhance Dengue protein expression (FIG. 5). Additionally, a higher cell density was observed in TRex cells expressing the codon optimized chimera DENV2/4opt, suggesting that expression of codon optimized CprME is less toxic to these cells. DsRed was used as a positive control for transfection efficiency.

EXAMPLE 7

RVP Infectivity from chimeric and codon-optimized DENV plasmids RVPs for DENV4 wt, and chimeras DENV2/4 wt, DENV2/4opt and DENV2/3opt were produced by calcium phosphate transfection of a GFP replicon plasmid (Ansarah-Sobrinho et al.) into 293 Trex stable CprME cell lines. Transfections were done in the absence of doxycycline, as over-expression of Dengue structural proteins in the absence of replicon is toxic to the cell. 4-8 hours post-transfection, the media was replaced with complete medium (DMEM-10% FCS, 1% penicillin/streptomycin solution, 2 mM L-alanyl L-glutamine solution, 25 mM HEPES, pH 8.0). 3 days post-transfection, Trex cells were induced to express CprME by the addition of doxyxycline (100 ng/ml) to the media. Cell supernatants containing RVPs were harvested at 24 hours (harvest A) post-induction. Harvested supernatants were passed through 0.45 μm syringe filters, aliquoted and frozen in a dry-ice ethanol bath for 15 minutes. RVPs were stored at −80° C. until needed. Raji DC-SIGN-R cells were infected with each of these RVPs. Particles produced by cells bearing the codon optimized DENV2/4 resulted in higher levels of infection (i.e. better RVP production) compared to those produced using either the DENV2/4 wt chimera or the DENV4 wt sequence (FIG. 6). In contrast, little to no increase was observed when comparing RVP production using the DENV2/4 wt chimera compared to the DENV4 wt. This experiment shows that the chimera alone is not sufficient for an increase in infectivity. However, in combination with codon optimization, chimerization results in increased infectivity when using stable cells for production.

EXAMPLE 8

Figure 9:
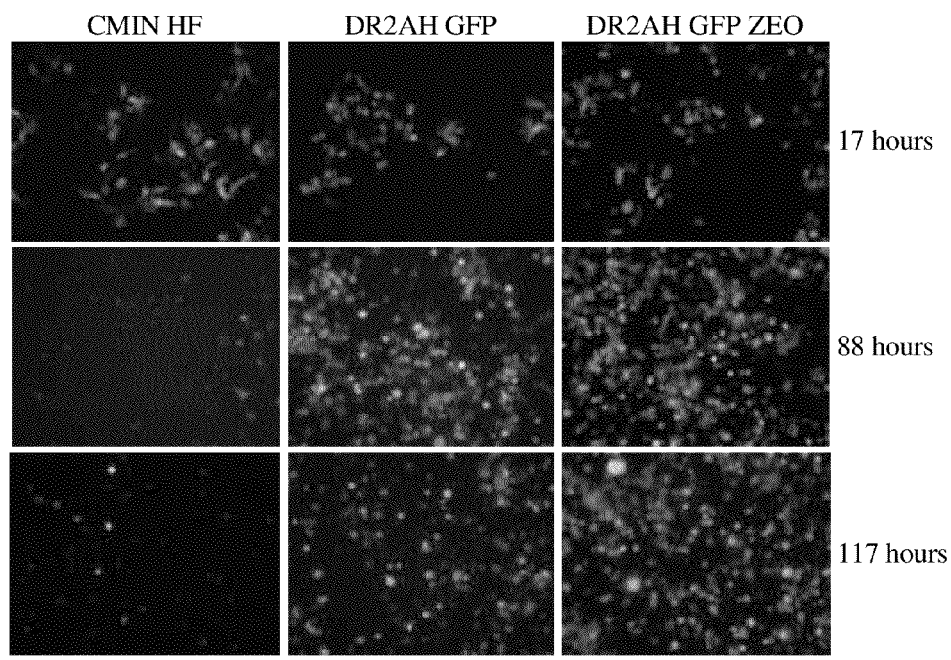
FIG. 9. GFP expression upon transfection of cells with plasmid encoding GFP or replicon. A. HEK-293T cells were plated in 6 well plates at a density of one million cells per well. Cells were transfected with the indicated plasmids using a standard lipofectamine 2000 transfection protocol. Plasmid "cmin HF" encodes a GFP protein under control of a minimal promoter. Plasmids pDR2AH GFP and pDR2AH GFP-Zeo carry dengue replicons that contain the GFP sequence. Cells were imaged using a Nikon Eclipse TE2000U microscope with a Coolpix camera. B. 293T cells were plated in 24 well plates at a density of $0.25 \times 10^6$ cells per well. Cells were transfected with the designated plasmids using a standard calcium phosphate protocol. At the indicated time points, cells were harvested, fixed with 2% paraformaldehyde, and analyzed by flow cytometry for GFP expression to obtain the mean fluorescence intensity.
Figure 9:
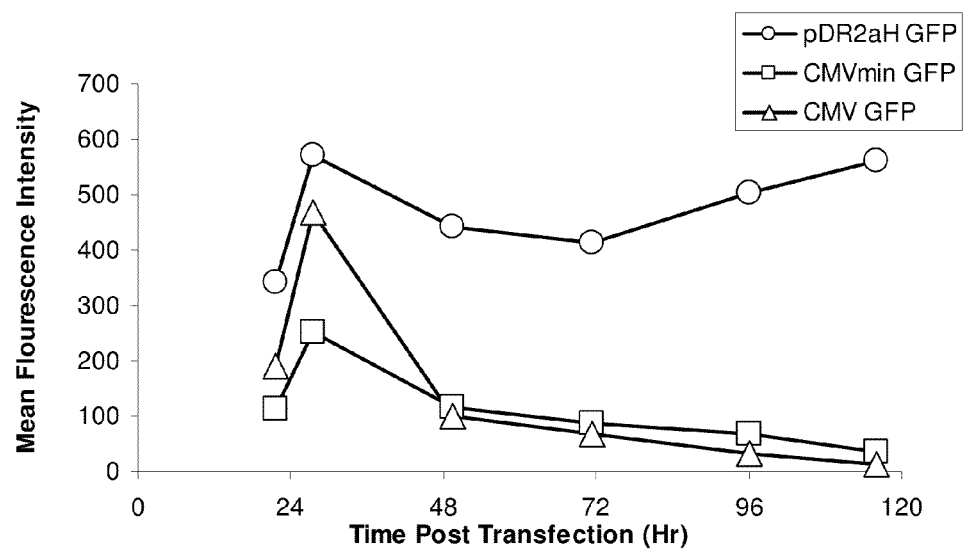

Production and neutralization of DENV RVPs. In order to produce infectious DENV RVPs, a replicon reporter plasmid encoding the non-structural genes of DENV and a complementary plasmid encoding the structural genes of DENV were co-expressed in cells. The replicon replicated within the cell, was packaged by the co-expressed structural components, and DENV RVPs were produced. Strains of RVPs representing all four serotypes of DENV were produced (FIG. 7A). RVP infection was readily detected using standard reporters (GFP or luciferase) expressed upon viral entry, and reporter signals were linearly proportional to the amount of RVPs added to cells. DENV RVPs were used to characterize the neutralizing (FIG. 7B) and enhancing activities of sera and isolated antibodies derived from vaccinated and naturally-infected individuals. The neutralization titers of monoclonal antibodies and sera derived using RVPs were statistically identical to titers obtained using conventional methodologies (e.g. the plaque reduction neutralization test, PRNT), suggesting that RVPs are antigenically equivalent to live DENV. Neutralization assays using dilutions of RVPs also suggest that little or no interfering antigen (e.g. free E protein or subviral particles) are present in RVP preparations, which is important for deriving accurate neutralization titers and for RVP capture assays. Upon delivery to a cell, the genomic replicon of the RVP expresses enzymatic proteins of the virus that facilitate genomic replication as well as high levels of reporter protein for extended periods of time. All studies suggest that DENV RVPs and the DENV replicon are functionally and antigenically equivalent to live DENV, enabling their use for the isolation of inhibitors against DENV.

EXAMPLE 9

Use of DENV reporter virus particles to detect a drug that inhibits entry. Raji-DC-SIGNR cells will be cultured in a 96-well plates at 30,000 cells per well. An equal volume of drug (or no drug control) will be added to the well at a 3× concentration before dilution with cells and RVPs (lx final in each well). An equal volume of RVPs are then added to the well and the plate will be returned to a 37° C., 5% CO2 incubator for 36-48 hours. Cells will then be analyzed for GFP expression by flow cytometry and percent GFP-positive cells determined. The extent of inhibition is calculated by dividing the (percent GFP-positive cells contacted drug) value by the (percent GFP-positive cells unexposed to drug) value. Other microplate formats (e.g. 384-well, 1536-well) could also be used. Other orders of addition of the cells and/or RVPs could also be performed.

EXAMPLE 10

Use of DENV reporter virus particles to detect a drug that inhibits assembly. CME expression cell lines will be cultured in 96-well plates. Cells will be transfected with replicon plasmid using calcium phosphate transfection or Lipofectamine transfection. Cells may be transfected either before or after addition to the microplates. At 72 hours post-transfection, the media will be changed on the cells to complete DMEM, pH 8 containing doxycycline and a different inhibitor in each well. Supernatants will be harvested from the producer cells at 96 hours post-transfection, frozen briefly, and then used to infect RajiDC-SIGNR cells. Approximately 48 hours after infection, the cells are fixed with 2% paraformaldehyde and analyzed by flow cytometry for the percentage of GFP positive cells.

EXAMPLE 11

Use of DENV reporter virus particles in high throughput screening. High-throughput assays using DENV RVPs and the dengue reporter replicon were used to identify inhibitors at each stage of the viral lifecycle. To monitor viral entry, RVPs carrying a luciferase reporter were incubated with permissive BHK-DC-SIGN cells followed by measurement of luciferase activity after 48 hours (FIG. 8A). Luciferase measurements from RVP infections in 384-well format were highly reproducible, with a Z'>0.5. To monitor dengue genomic replication, we generated a stable cell line carrying a DENV GFP replicon. Fluorescence measurements from these cells in 384-well format were highly reproducible (Z'>0.5). In proof-of-concept screening of random compounds (plus controls), compounds that inhibited replicon replication resulted in the attenuation of GFP and could be readily identified (FIG. 8B). To screen for compounds that inhibit viral assembly and budding, we developed an RVP production assay in which cells were co-transfected with a replicon and a plasmid expressing the DENV structural genes. Supernatants containing RVPs were harvested 2-3 days post-transfection and captured onto ConA lectin microplates, followed by quantitative detection by ELISA. DENV RVPs could be readily detected in the supernatants of transfected cells compared to control samples.

EXAMPLE 12

Use of a DENV replicon for sustained protein expression. Plasmids pGFP(CMV-driven GFP), pDR2AH GFP (replicon GFP), and pDR2AH GFP ZEO (replicon GFP) were transfected into HEK-293T cells using a standard calcium phosphate transfection method. Cell culture media was changed approximate 4-16 hours post-transfection. Cells were examined for GFP expression visually using a fluorescent microscope. Both replicon pDR2AH GFP and pDR2AH GFPZeo resulted in GFP expression in target cells (FIG. 9, Panel A). Cells transfected with pGFP or pDR2AH GFP were analyzed by flow cytometry at multiple time points post-transfection. Prolonged GFP expression was observed in pDR2AH GFP replicon-transfected cells for at least 117 h post-transfection, after it was no longer observed in pGFP plasmid transfected cells (FIG. 9, Panel B), indicating productive replication of the GFP replicon within the cells. The replicon could thus be used to obtain sustained protein expression in cells, including cells in culture and cells in animals. In one manifestation, the replicon is used as a DNA vaccine to express antigenic proteins in humans or other animals for prolonged periods of time to generate a protective immune response.

---

What is claimed is:

1. An isolated nucleic acid molecule comprising a nucleic acid molecule that comprises a sequence that is at least 95% identical to a sequence comprising SEQ ID NO: 1 or SEQ ID NO: 3.

2. The isolated nucleic acid molecule of claim 1, wherein said nucleic acid molecule is operably linked to a constitutively active mammalian promoter.

3. A plasmid comprising the nucleic acid molecule of claim 1.

4. An isolated cell comprising the nucleic acid molecule of claim 1.

5. The isolated cell of claim 4 further comprising a DENV2 replicon.

6. The isolated cell of claim 4, wherein said cell further comprises a flavivirus NS3 protein.

7. A method of producing a dengue reporter virus particle comprising transfecting a producer cell with a plasmid DNA molecule comprising a nucleic acid molecule comprising SEQ ID NO: 1 or 3 and optionally isolating the reporter virus particles in the supernatant from said transfected producer cell,
wherein said producer cell takes up the plasmid DNA molecule, expresses a replicon of DEN, and produces DENV RVPs that are released from said producer cell.

8. The nucleic acid molecule of claim 1, wherein said nucleic acid molecule is at least 99% identical to a sequence comprising SEQ ID NO: 1 or SEQ ID NO: 3.

9. The nucleic acid molecule of claim 1, wherein said nucleic acid molecule is at least 98% identical to a sequence comprising SEQ ID NO: 1 or SEQ ID NO: 3.

10. The nucleic acid molecule of claim 1, wherein said nucleic acid molecule comprises SEQ ID NO: 1 or SEQ ID NO: 3.

11. A plasmid comprising the nucleic acid molecule of claim 2.

12. A plasmid comprising the nucleic acid molecule of claim 8.

13. The plasmid of claim 12, wherein the nucleic acid molecule is operably linked to a constitutively active mammalian promoter.

14. A plasmid comprising the nucleic acid molecule of claim 9.

15. The plasmid of claim 14, wherein the nucleic acid molecule is operably linked to a constitutively active mammalian promoter.

16. A plasmid comprising the nucleic acid molecule of claim 10.

* * * * *